United States Patent
Trotter et al.

(10) Patent No.: US 10,689,708 B2
(45) Date of Patent: Jun. 23, 2020

(54) METHODS FOR TREATING DIFFUSE LARGE B-CELL LYMPHOMA AND THE USE OF BIOMARKERS AS A PREDICTOR OF RESPONSIVENESS TO DRUGS

(71) Applicant: Celgene Corporation, Summit, NJ (US)

(72) Inventors: Matthew William Burnell Trotter, Espartinas (ES); Alberto Risueno Perez, Seville (ES); Michael Pourdehnad, San Francisco, CA (US); Anita Gandhi, Bernardsville, NJ (US); Patrick Hagner, Sparta, NJ (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 15/273,205

(22) Filed: Sep. 22, 2016

(65) Prior Publication Data

US 2017/0088901 A1 Mar. 30, 2017

Related U.S. Application Data

(60) Provisional application No. 62/324,829, filed on Apr. 19, 2016, provisional application No. 62/233,181, filed on Sep. 25, 2015.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
CPC ............ C12Q 1/6886; C12Q 2600/158; C12Q 2600/106
See application file for complete search history.

(56) References Cited

U.S. PATENT DOCUMENTS

| | | | |
|---|---|---|---|
| 7,655,444 B2 | 2/2010 | Herman et al. | |
| 7,893,045 B2 * | 2/2011 | Pietronigro | A61K 31/454 514/183 |
| 9,365,640 B2 | 6/2016 | Lopez-Girona et al. | |
| 9,857,359 B2 | 1/2018 | Schafer et al. | |
| 10,047,151 B2 | 8/2018 | Lopez-Girona et al. | |
| 2005/0164231 A1 * | 7/2005 | Staudt | C12Q 1/6886 435/6.16 |
| 2012/0123695 A1 | 5/2012 | Dornan et al. | |
| 2012/0322073 A1 * | 12/2012 | Lopez-Girona | C07K 16/18 435/6.12 |
| 2014/0045843 A1 * | 2/2014 | Schafer | A61K 31/5377 514/235.2 |
| 2014/0162282 A1 | 6/2014 | Schafer et al. | |
| 2014/0220562 A1 | 8/2014 | Alizadeh et al. | |
| 2014/0328832 A1 * | 11/2014 | Chopra | A61K 31/505 424/133.1 |
| 2016/0312292 A1 | 10/2016 | Trotter | |
| 2016/0313300 A1 | 10/2016 | Trotter et al. | |
| 2016/0319005 A1 | 11/2016 | Lopez-Girona et al. | |
| 2016/0356778 A1 | 12/2016 | Iha et al. | |
| 2017/0038387 A1 | 2/2017 | Gandhi et al. | |
| 2017/0199193 A1 | 7/2017 | Filvaroff et al. | |
| 2017/0242014 A1 | 8/2017 | Hagner et al. | |
| 2018/0209961 A1 | 7/2018 | Schafer et al. | |
| 2018/0231561 A1 | 8/2018 | Gandhi et al. | |
| 2019/0004033 A1 | 1/2019 | Trotter et al. | |

FOREIGN PATENT DOCUMENTS

| | | | |
|---|---|---|---|
| WO | WO-2015085160 A2 * | 6/2015 | ........... C12Q 1/6886 |
| WO | WO-2015085172 A2 * | 6/2015 | ......... G01N 33/6863 |
| WO | WO 2015085172 A2 | 6/2015 | |
| WO | WO 2015085172 A3 | 6/2015 | |
| WO | WO 2017027672 A1 | 2/2017 | |

OTHER PUBLICATIONS

Celgene. Dec. 8, 2014. Retrieved on Jan. 31, 2017 from the internet: http://files.shareholder.com/downloads/AMDA-262QUJ/5945720814x0x798447/C8942732-020E-4884-B3F4-82BE8C349467/CELG_News_2014_12_8_General_Releases.pdf. (Year: 2014).*
Chen et al. Molecular & Cellular Proteomics 1.4. 2001. MCP Papers in Press. (Year: 2001).*
Kendrick. Kendrick Labs, Inc. Updated Sep. 25, 2014. (Year: 2014).*
Maier et al. FEBS Letters. 2009. 583:3966-3973. (Year: 2009).*
Pascal et al. BMC Genomics. 2008. 9:246. (Year: 2008).*
Chan et al. G&P magazine. 2006. 6(3): 20-26. (Year: 2006).*
Cheung et al. Nature Genetics. 2003. 33:422-425. (Year: 2003).*
Dai et al., "Extracellular signal-regulated kinase positively regulates the oncogenic activity of MCT-1 in diffuse large B-cell lymphoma", Cancer Res., 69(19):7835-7843 (2009).
International Search Report and Written Opinon dated Dec. 7, 2016 in correspondeing PCT Application No. PCT/US2016/053092 (9 pages).

* cited by examiner

*Primary Examiner* — Joseph G. Dauner
(74) *Attorney, Agent, or Firm* — Jones Day

(57) ABSTRACT

In one aspect, provided herein are methods for predicting the responsiveness of DLBCL patients to treatment with lenolidomide or Compound A; or a stereoisomer thereof; or a pharmaceutically acceptable salt, solvate, hydrate, co-crystal, clathrate thereof; or a polymorph thereof utilizing biomarkers or classifiers that correlate with responsiveness to one of these drugs. In another aspect, provided herein are methods for treating a DLBCL patient determined to be responsive to treatment with lenolidomide or Compound A; or a stereoisomer thereof; or a pharmaceutically acceptable salt, solvate, hydrate, co-crystal, clathrate thereof; or a polymorph thereof utilizing biomarkers or classifiers (or output thereof) that correlate with responsiveness to one of these drugs.

11 Claims, 9 Drawing Sheets

METHODS FOR TREATING DIFFUSE LARGE B-CELL LYMPHOMA AND THE USE OF BIOMARKERS AS A PREDICTOR OF RESPONSIVENESS TO DRUGS

CROSS-REFERENCES TO RELATED APPLICATIONS

This application claims the benefit of priority to U.S. Ser. No. 62/233,181 filed Sep. 25, 2015 and U.S. Ser. No. 62/324,829 filed Apr. 19, 2016, each of which is herein incorporated by reference in their entirety.

1. FIELD

In one aspect, provided herein are methods for predicting the responsiveness of DLBCL patients to treatment with lenolidomide or Compound A; or a stereoisomer thereof; or a pharmaceutically acceptable salt, solvate, hydrate, co-crystal, clathrate thereof; or a polymorph thereof utilizing biomarkers or classfiers that correlate with responsiveness to one of these drugs. In another aspect, provided herein are methods for treating a DLBCL patient determined to be responsive to treatment with lenolidomide or Compound A; or a stereoisomer thereof; or a pharmaceutically acceptable salt, solvate, hydrate, co-crystal, clathrate thereof; or a polymorph thereof utilizing biomarkers or classifiers (or output thereof) that correlate with responsiveness to one of these drugs.

2. BACKGROUND

2.1 Pathobiology of DLBCL

The non-Hodgkin lymphomas (NHLs) are a diverse group of blood cancers that include any kind of lymphoma except Hodgkin's lymphomas. Types of NHL vary significantly in their severity, from indolent to very aggressive. Less aggressive non-Hodgkin lymphomas are compatible with a long survival while more aggressive non-Hodgkin lymphomas can be rapidly fatal without treatment. They can be formed from either B-cells or T-cells. B-cell non-Hodgkin lymphomas include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. T-cell non-Hodgkin lymphomas include mycosis fungoides, anaplastic large cell lymphoma, and precursor T-lymphoblastic lymphoma. Prognosis and treatment depend on the stage and type of disease.

Diffuse large B-cell lymphoma (DLBCL) accounts for approximately one-third of non-Hodgkin's lymphomas. While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma.

The diffuse large B-cell lymphomas (DLBCL) can be divided into distinct molecular subtypes according to their gene profiling patterns: germinal-center B-cell-like DLBCL (GCB-DLBCL), activated B-cell-like DLBCL (ABC-DLBCL), and primary mediastinal B-cell lymphoma (PMBL) or unclassified type. These subtypes are characterized by distinct differences in survival, chemo-responsiveness, and signaling pathway dependence, particularly the NF-κB pathway. See D. Kim et al., *Journal of Clinical Oncology*, 2007 ASCO Annual Meeting Proceedings Part I. Vol 25, No. 18S (June 20 Supplement), 2007: 8082. See Bea S, et al., *Blood* 2005; 106: 3183-90; Ngo V. N. et al., *Nature* 2011; 470: 115-9. Such differences have prompted the search for more effective and subtype-specific treatment strategies in DLBCL.

The incidence of cancer continues to climb as the general population ages, as new cancers develop, and as susceptible populations grow. A tremendous demand therefore exists for new methods and compositions that can be used to treat patients with NHL including DLBCL.

2.2. Methods of Treatment

Current cancer therapy, in general, can involve surgery, chemotherapy, hormonal therapy and/or radiation treatment to eradicate neoplastic cells in a patient (see, for example, Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove refractory to standard chemotherapeutic treatment protocols.

In the context of DLBCL, treatment usually includes administration of a combination of chemotherapy and antibody therapy. The most widely used treatment of DLBCL is a mixture of the antibody rituximab and several chemotherapy drugs (cyclophosphamide, doxorubicin, vincristine, and prednisone (R-CHOP), and in some cases etoposide is added (R-EPOCH)). DLBCL also typically requires immediate treatment upon diagnosis due to how quickly the disease can advance. For some patients, DLBCL returns or becomes refactory following treatment. Several alternative treatments, some of which can include use of lenalidomide, are currently being tested in clinical trials for patients with newly diagnosed, relapsed or refractory DLBCL.

Thus, there is a significant need for safe and effective methods of treating, preventing and managing cancer including DLBCL, particularly for cancers that are refractory to standard treatments, such as surgery, radiation therapy, chemotherapy and hormonal therapy, while reducing or avoiding the toxicities and/or side effects associated with the conventional therapies. Moreover, there remains a need for the ability to predict and monitor response to therapy in order to increase the quality of care for patients, avoid unnecessary treatment and to increase the success rate in treating cancer, including DLBCL, in clinical practice.

3. SUMMARY

The present disclosure is based, in part, on the discovery that DLBCL patient pre-treatment transcriptional profiles derived from tumor biopsies can be used to predict responsiveness of future DLBCL patients to treatment with lenalidomide and/or Compound A.

In one aspect, provided herein are methods for predicting responsiveness of a DLBCL patient to a drug comprising: (a) obtaining a first biological sample from a first patient having a DLBCL; (b) determining the level of expression of one, two, three, four, five or more of the genes identified in Table 1, 2, and/or 3; (c) comparing the level of expression of the one, two, three, four, five or more of the genes identified in Table 1, 2, and/or 3 in the first biological sample with the level of expression of the same genes in a second biological sample(s) from a second patient(s), wherein the second DLBCL patient(s) is not responsive to the drug, and wherein the differential expression of the one, two, three, four, five or more of the genes in the first biological sample relative to the level of expression of the one, two, three, four, five or more of the genes in the second biological sample(s) indicates that the DLBCL in the first patient will be responsive to treatment with the drug, wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof, or a pharmaceutically acceptable salt, solvate, hydrate, co-crystal, clathrate thereof; or a polymorph thereof.

In some embodiments, provided herein are methods for predicting responsiveness of a DLBCL patient to a drug comprising: (a) obtaining a first biological sample from a first patient having a DLBCL; (b) determining the level of expression of one, two, three, four, five or more of the genes identified in Table 1, 2, and/or 3; (c) comparing the level of expression of the one, two, three, four, five or more of the genes identified in Table 1, 2, and/or 3 in the first biological sample with the level of expression of the same genes in a second biological sample(s) from a second patient(s), wherein the second DLBCL patient(s) is responsive to the drug, and wherein the similar expression of the one, two, three, four, five or more of the genes in the first biological sample relative to the level of expression of the one, two, three, four, five or more of the genes in the second biological sample(s) indicates that the DLBCL in the first patient will be responsive to treatment with the drug, wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof, or a pharmaceutically acceptable salt, solvate, hydrate, co-crystal, clathrate thereof; or a polymorph thereof.

In another aspect, provided herein are methods for predicting responsiveness of a DLBCL patient to a drug comprising: (a) obtaining a first biological sample from a first DLBCL patient; (b) determining the expression of the genes or a certain subset of genes set forth in Table 1, 2, and/or 3, or any combination thereof, in the first biological sample; and (c) comparing the gene expression profile of the genes or subset of genes in the first biological sample to (i) the gene expression profile of the genes or subset of genes in biological samples from DLBCL patients which are responsive to the drug and (ii) the gene expression of the genes or subset of genes in biological samples from DLBCL patients which are not responsive to the drug, wherein a gene expression profile for the genes or subset of genes in the first biological sample similar to the gene expression profile for the genes or subset of genes in biological samples from DLBCL patients which are responsive to the drug indicates that the first DLBCL patient will be responsive to treatment with the drug, and a gene expression profile for the genes or subset of genes in first biological sample similar to the gene expression profile for the genes or subset of genes in biological samples from DLBCL patients which are not responsive to the drug indicates that the first DLBCL patient will not be responsive to treatment with the drug, wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof; or a pharmaceutically acceptable salt, solvate, hydrate, co-crystal, clathrate thereof; or a polymorph thereof. In some embodiments, the subset(s) of genes are a subset(s) of those genes in Table 1, a subset(s) of those genes in Table 2, and/or a subset(s) of those genes in Table 3.

In another aspect, provided herein are methods for predicting responsiveness of a DLBCL patient to a drug comprising: (a) obtaining a first biological sample from a first DLBCL patient; (b) determining the expression of the genes or a certain subset of genes set forth in Table 1, 2 and/or 3, or any combination thereof, in the first biological sample and generating a score based on the expression of the genes or subset of genes, (c) comparing the score to a reference score, wherein a score similar to a reference score indicates that the patient will be responsive to treatment with the drug. In specific embodiments, the reference score is based on the expression of the same genes or subset of genes in a population of DLBCL patients responsive to the drug. In a specific embodiment, the drug is a compound disclosed herein.

In another aspect, provided herein are methods for predicting responsiveness of a DLBCL patient with a drug comprising: (a) obtaining a first biological sample from a first DLBCL patient; (b) determining the expression of the genes or a certain subset of genes set forth in Table 1, 2 and/or 3, or any combination thereof, in the first biological sample and generating a score based on the expression of the genes or subset of genes, (c) comparing the score to a first reference score and a second reference score, wherein a score similar to the first reference score indicates that the patient will be responsive to the treatment with the drug. In specific embodiments, the first reference score is based on the expression of the same genes or subset of genes in a population of DLBCL patients responsive to the drug and the second reference score is based on the expression of the same genes or subset of genes in a population of DLBCL patients not responsive to the drug. In a specific embodiment, the drug is a compound disclosed herein.

In yet another aspect, provided herein are methods for treating a DLBCL patient with a drug comprising: (a) obtaining a first biological sample from a first DLBCL patient; (b) determining the level of expression of one, two, three, four, five or more of the genes identified in Table 1, 2, and/or 3; (c) comparing the level of expression of the one, two, three, four, five or more of the genes identified in Table 1, 2, and/or 3 in the first biological sample with the level of expression of the same genes in a second biological sample(s) from a second DLBCL patient(s), wherein the second DLBCL patient is not responsive to the drug; and (d) administering the drug to the first patient if the one, two, three, four, five or more of the genes in the first biological sample are differentially expressed relative to the level of expression of the one, two, three, four, five or more of the genes in the second biological sample(s), wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof; or a pharmaceutically acceptable salt, solvate, hydrate, co-crystal, clathrate thereof; or a polymorph thereof.

In some embodiments, provided herein are methods for treating a DLBCL patient with a drug comprising: (a) obtaining a first biological sample from a first DLBCL patient; (b) determining the level of expression of one, two, three, four, five or more of the genes identified in Table 1, 2, and/or 3; (c) comparing the level of expression of the one, two, three, four, five or more of the genes identified in Table 1, 2, and/or 3 in the first biological sample with the level of expression of the same genes in a second biological sample(s) from a second DLBCL patient(s), wherein the second DLBCL patient is responsive to the drug; and (d) administering the drug to the first patient if the one, two, three, four, five or more of the genes in the first biological sample are similarly expressed relative to the level of expression of the one, two, three, four, five or more of the genes in the second biological sample(s), wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof; or a pharmaceutically acceptable salt, solvate, hydrate, co-crystal, clathrate thereof; or a polymorph thereof.

In still another aspect, provided herein are methods for treating a DLBCL patient with a drug comprising: (a) obtaining a first biological sample from a first DLBCL patient; (b) determining the expression of the genes or a certain subset of genes set forth in Table 1, 2 and/or 3, or any combination thereof, in the first biological sample, (c) comparing the gene expression profile of the genes or the subset of genes in the first biological sample to (i) the gene expression profile of the genes or the subset of genes in biological samples from DLBCL patients which are responsive to the drug and (ii) the gene expression of the genes or the subset of genes in biological samples from DLBCL patients which are not responsive to the drug; and (d) administering the drug to the first patient if: (i) the gene expression profile for the genes or the subset of genes in the first biological sample is similar to the gene expression profile for the genes or the subset of genes in biological samples from DLBCL patients which are responsive to the drug and (ii) the gene expression profile for the genes or the subset of genes in first biological sample is not similar to the gene expression profile for the genes or the subset of genes in biological samples from DLBCL patients which are not responsive to the drug, wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof, or a pharmaceutically acceptable salt, solvate, hydrate, co-crystal, clathrate thereof; or a polymorph thereof. In some embodiments, the subset(s) of genes are a subset(s) of those genes in Table 1, a subset(s) of those genes in Table 2, and/or a subset(s) of those genes in Table 3.

In some embodiments of the various methods provided herein, expression levels of multiple genes (biomarkers) provided herein are used to predict a patient's response to the compound provided herein. When expression levels of multiple genes (biomarkers) are used to predict a patient's response to a treatment with the compound provided herein, e.g., lenalidomide and Compound A, any classifier that classifies based on two or more features can be used in the present disclosure.

In some embodiments, the methods provided herein further comprise (a) generating a score of the sample based on the expression levels of the genes or a subset thereof provided herein in the sample; and (b) determining the probability of the subject being responsive to the compound provided herein by comparing the score of the sample to a reference score.

In some more specific embodiments, the methods provided herein further comprise: (a) determining the expression levels of the genes or a subset thereof provided herein in a biological sample from a population of subjects that previously have been administered with the compound provided herein, (b) generating a score for the expression levels of the genes or a subset thereof provided herein for each subject of the population; (c) differentiating the subjects that are responsive to the compound provided herein from those subjects that are not responsive to the compound provided herein; and (d) determining responsiveness to the compound provided herein based on the scores for the subjects that are responsive to the compound and those subjects that are not responsive to the compound.

In other more specific embodiments, the methods provided herein further comprise: (a) determining the expression levels of the genes or a subset thereof provided herein in a biological sample from a population of subjects that previously have been administered with the compound, (b) generating a score for the expression levels of the genes or a subset thereof provided herein for each subject of the population; (c) differentiating the subjects that are responsive to the compound provided herein from those subjects that are not responsive to compound provided herein; and (d) generating a reference score that is predictive of the responsiveness of a subject to the compound provided herein using a model based on the scores for the subjects that are responsive to the compound and those subjects that are not responsive to the compound.

In another aspect, provided herein are methods for treating a DLBCL patient with a drug comprising: (a) obtaining a first biological sample from a first DLBCL patient; (b) determining the expression of the genes or a certain subset of genes set forth in Table 1, 2 and/or 3, or any combination thereof, in the first biological sample and generating a score based on the expression of the genes or subset of genes, (c) comparing the score to a reference score; and (d) administering the drug to the first patient if the score is similar to the reference score. In specific embodiments, the reference score is based on the expression of the same genes or subset of genes in a population of DLBCL patients responsive to the drug. In a specific embodiment, the drug is a compound disclosed herein.

In another aspect, provided herein are methods for treating a DLBCL patient with a drug comprising: (a) obtaining a first biological sample from a first DLBCL patient; (b) determining the expression of the genes or a certain subset of genes set forth in Table 1, 2 and/or 3, or any combination thereof, in the first biological sample and generating a score based on the expression of the genes or subset of genes, (c) comparing the score to a first reference score and a second reference score; and (d) administering the drug to the first patient if the score is similar to the first reference score. In specific embodiments, the first reference score is based on the expression of the same genes or subset of genes in a population of DLBCL patients responsive to the drug and the second reference score is based on the expression of the same genes or subset of genes in a population of DLBCL patients not responsive to the drug. In a specific embodiment, the drug is a compound disclosed herein.

4. BRIEF DESCRIPTION OF THE FIGURES

FIG. 1 shows illustrative Kaplan-Meier plot of Investigator-determined PFS for 21 patients in the lenalidomide-arm of REV-DLC-001, stratified according to prediction made by SVM-RFE classifier trained on pseudo-labeled published DLBCL gene expression profiles based on the genes of Table 1. The upper survival curve describes PFS for the 6 patients predicted as belonging to the putative positive outcome group. The lower survival curve describes PFS for the remaining 15 patients (putative negative outcome group). Log-rank test of difference between survival distributions, p=0.049.

FIG. 2 shows illustrative Kaplan-Meier plot of Investigator-determined PFS for 21 patients in the lenalidomide-arm of REV-DLC-001, stratified according to prediction made by SVM-RFE classifier trained on the pseudo-labeled published DLBCL gene expression profiles based on the genes of Table 2. The upper survival curve describes PFS for the 7 patients predicted as belonging to the putative positive outcome group. The lower survival curve describes PFS for the remaining 14 patients (putative negative outcome group). Log-rank test of difference between survival distributions, p=0.013.

5. DETAILED DESCRIPTION OF THE INVENTION

5.1 Terminology

Figure 1:
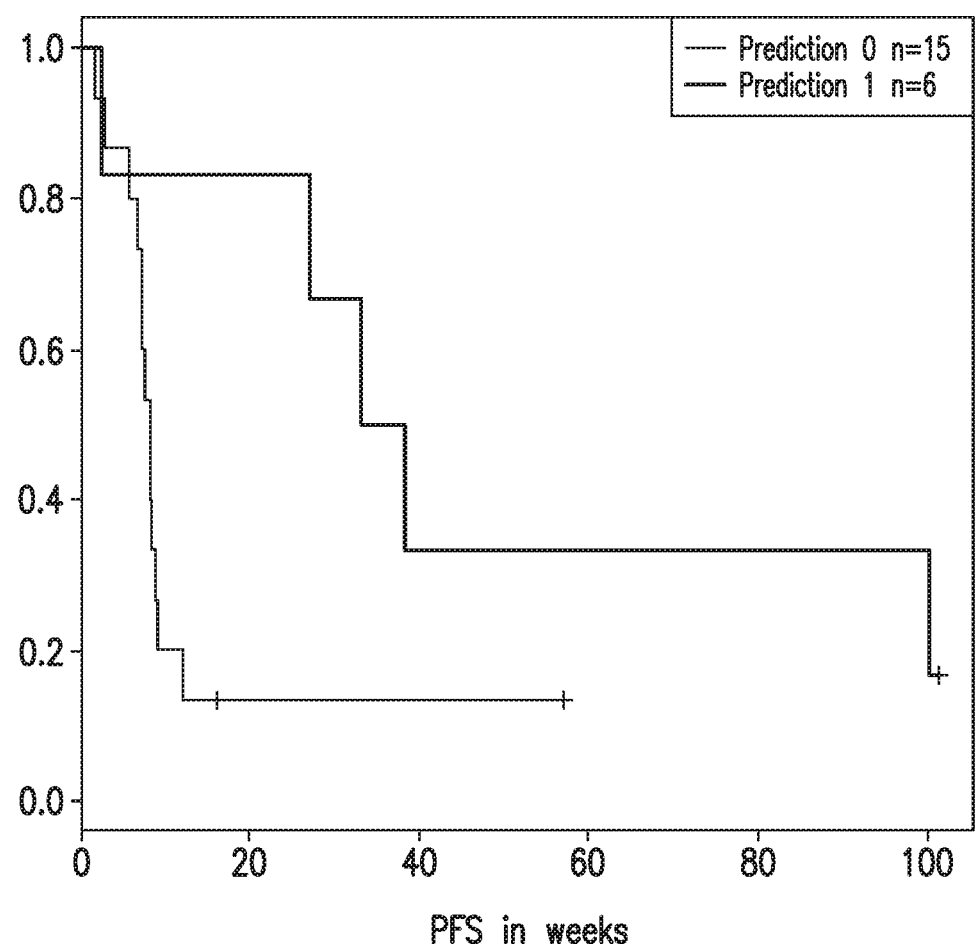

The use of the word "a" or "an" when used in conjunction with the term "comprising" in the claims and/or the specification can mean "one," but it is also consistent with the meaning of "one or more," "at least one," and "one or more than one."

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 20%, 15%, 10%, 9%, 8%, 7%, 6%, 5%, 4%, 3%, 2%, 1%, 0.5%, or 0.05% of a given value or range.

As used herein, unless otherwise specified or indicated from context, the term "pre-treatment" as used in accordance with the methods described herein refers to prior to administration of a drug.

As used herein, unless otherwise specified or indicated from context, the terms "drug" and "compound" refer to a drug described in Section 5.4, infra.

As used herein, the terms "patient" and "subject" refer to an animal, such as a mammal. In a specific embodiment, the patient is a human. In other embodiments, the patient is a non-human animal, such as a dog, cat, farm animal (e.g., horse, pig, or donkey), chimpanzee, or monkey. In specific embodiments, the patient is a human with DLBCL in need of treatment.

As used herein, and unless otherwise specified, the terms "treat," "treating" and "treatment" refer to an action that occurs while a patient is suffering from DLBCL. Treatment with a drug may results in, e.g., one, two or more of the following: reduction in the severity of the cancer, reduction in tumor size, or retardation or slowing the progression of DLBCL, increase in progression free survival, increase in time to tumor progression, and/or improvement in one or more symptoms or treatment outcomes such as complete response or partial response.

The term "complex," when used in reference to detection of gene expression, refers to a molecule in which one or more groups are linked by bonds, which includes a non-naturally occurring molecule that is dependent upon the presence of the gene product (RNA and/or protein) in a sample. For example, a complex can include, but is not limited to, a hybridization complex, an enzyme-substrate complex, or an antibody-antigen complex. A "hybridization complex" refers to the interaction of two or more nucleic acid molecules by intermolecular forces including, but not limited to, covalent or non-covalent bonds, Van der Waals forces, dipole-dipole interactions, hydrogen bonding, and London dispersion forces.

The phrase "reaction product," when used in reference to detection of gene expression, refers to a substance that is formed as a result of a chemical or biological reaction that is dependent upon the presence of the target substrate in a sample. In some embodiments, the reaction product is a non-naturally occurring molecule. Such a non-naturally occurring molecule can be the result of methods well-known in the art for detecting gene expression. Such methods include, but are not limited to, polymerase chain reaction (PCR) based methods including quantitative real-time PCR (qPCR), reverse transcription PCR (RT-PCR) and reverse transcription qPCR (RT-qPCR), physical property assays (e.g., gel electrophoresis, Northern blot, Western blot), fluorescent in situ hybrization, serial analysis of gene expression (SAGE), Whole Transcriptome Shotgun Sequencing (WTSS), deep sequencing, microarrays/gene chips, digital gene expression analysis (e.g., NanoString assay), flow cytometry, immunofluorscence, and enzyme-linked immunosorbent assay-based methodologies (ELISA).

By "solid support," "solid substrate" or other grammatical equivalents herein refers to any material that contains and/or can be modified to contain one or more sites (e.g., discrete individual sites, pre-defined sites, random sites, etc.) appropriate for the attachment or association of compositions disclosed herein and is amenable to at least one detection method. As will be appreciated by those in the art, there are many possible substrates. Possible substrates include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, resins, silica or silica-based materials (including silicon and modified silicon), carbon, metals, inorganic glasses, plastics, optical fiber bundles, and a variety of other polymers. In general, the substrates can allow optical detection and do not themselves appreciably fluoresce.

A solid support can be flat (planar), although as will be appreciated by those in the art, other configurations of substrates may be used as well; for example, three dimensional configurations can be used, for example by embedding beads in a porous block of plastic that allows sample access to the beads and using a confocal microscope for detection. Similarly, the beads may be placed on the inside surface of a tube, for flow-through sample analysis to minimize sample volume. In some aspects substrates include optical fiber bundles and flat planar substrates such as glass, polystyrene and other plastics and acrylics. A bead includes a small discrete particle, the composition of which will depend on the class of probe used and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon® may all be used. "Microsphere Detection Guide" from Bangs Laboratories, Fishers Ind. is a helpful guide.

A "label" or the phrase "detectably labeled" when used in reference to a complex or reaction product, refers to a composition that, when linked with a complex or reaction product, renders the complex or reaction product detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled complex" or "labeled reaction product" is generally one that is bound, either covalently, through a linker or a chemical bond, or noncovalently, through ionic bonds, van der Waals forces, electrostatic attractions, hydrophobic interactions, or hydrogen bonds, to a label such that the presence of the complex or reaction product can be detected by detecting the presence of the label bound to the complex or reaction product.

As used herein, and unless otherwise specified, the term "effective amount" of a compound is an amount sufficient to provide a therapeutic benefit in the treatment of DLBCL, or to delay or minimize one or more symptoms associated with the presence of DLBCL. The term "effective amount" can encompass an amount that improves overall therapy, reduces or avoids symptoms or causes of DLBCL, or enhances the therapeutic efficacy of another therapeutic agent. In certain embodiments, an effective amount of a drug improves overall survival, disease free survival, objective response rate, time to tumor progression, progression free survival or time-to-treatment failure. In some embodiments, an effective amount of a drug results in a partial response or complete response.

The term "responsiveness" or "responsive" when used in reference to a treatment refers to the degree of effectiveness of treatment with the drug for a DLBCL patient. For example, the term "increased responsiveness" when used in reference to treatment of a DLBCL patient can refer to an increase in the effectiveness of the drug when measured using any methods known in the art. As another example, response of a DLBCL patient to the drug can be characterized as a complete or partial response. As another example, increased responsiveness of a DLBCL patient to the drug can be characterized as overall survival, disease free survival, objective response rate, time to tumor progression, progression free survival or time-to-treatment failure. "Responsiveness" or "response" to a treatment as used herein can also refer to displaying phenotypic physical or molecular characteristics associated with a compound treatment. "Responsiveness" or "response" to a DLBCL treatment as used herein can be determined based on reduced symptoms associated with DLBCL, such as fever, weight loss, or night sweats. In some embodiments, whether a DLBCL patient is responsive to a treatment is determined by staging tests, which are tests helpful for determining which areas of the body have been affected by follicular lymphoma. Such tests include, but not limited to, blood tests, bone marrow biopsy, CT scan, and PET/CT scan. Staging involves dividing patients into groups (stages) based upon how much of the lymphatic system is involved. Stages of lymphoma can be defined as follows: stage I—only one lymph node region is involved, only one lymph structure is involved, or only one extranodal site (IE) is involved; stage II—two or more lymph node regions or lymph node structures on the same side of the diaphragm are involved; stage III—lymph node regions or structures on both sides of the diaphragm are involved; stage IV—there is widespread involvement of a number of organs or tissues other than lymph node regions or structures, such as the liver, lung, or bone marrow. A lymph node region refers to an area of lymph nodes and the surrounding tissue, e.g., the cervical nodes in the neck, the axillary nodes in the armpit, the inguinal nodes in the groin, and the mediastinal nodes in the chest. A lymph structure refers to an organ or a structure that is part of the lymphatic system, such as the lymph nodes, spleen, and thymus gland.

"Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in any measurable tumor burden (i.e., the number of malignant cells present in the subject, or the measured bulk of tumor masses or the quantity of abnormal monoclonal protein) in the absence of new lesions.

"Overall survival" is defined as the time from randomization until death from any cause, and is measured in the intent-to-treat population. Overall survival should be evaluated in randomized controlled studies. Demonstration of a statistically significant improvement in overall survival can be considered to be clinically significant if the toxicity profile is acceptable, and has often supported new drug approval.

Several endpoints are based on tumor assessments. These endpoints include disease free survival (DFS), objective response rate (ORR), time to progression (TTP), progression-free survival (PFS), and time-to-treatment failure (TTF). The collection and analysis of data on these time-dependent endpoints are based on indirect assessments, calculations, and estimates (e.g., tumor measurements).

Generally, "disease free survival" (DFS) is defined as the time from randomization until recurrence of tumor or death from any cause. Although overall survival is a conventional endpoint for most adjuvant settings, DFS can be an important endpoint in situations where survival may be prolonged, making a survival endpoint impractical. DFS can be a surrogate for clinical benefit or it can provide direct evidence of clinical benefit. This determination is based on the magnitude of the effect, its risk-benefit relationship, and the disease setting. The definition of DFS can be complicated, particularly when deaths are noted without prior tumor progression documentation. These events can be scored either as disease recurrences or as censored events. Although all methods for statistical analysis of deaths have some limitations, considering all deaths (deaths from all causes) as recurrences can minimize bias. DFS can be overestimated using this definition, especially in patients who die after a long period without observation. Bias can be introduced if the frequency of long-term follow-up visits is dissimilar between the study arms or if dropouts are not random because of toxicity.

"Objective response rate" (ORR) is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study. If available, standardized criteria should be used to ascertain response. A variety of response criteria have been considered appropriate (e.g., RECIST criteria) (Therasse et al., (2000) J. Natl. Cancer Inst, 92: 205-16). The significance of ORR is assessed by its magnitude and duration, and the percentage of complete responses (no detectable evidence of tumor).

"Time to progression" (TTP) and "progression-free survival" (PFS) have served as primary endpoints for drug approval. TTP is defined as the time from randomization until objective tumor progression; TTP does not include deaths. PFS is defined as the time from randomization until objective tumor progression or death. Compared with TTP, PFS is the preferred regulatory endpoint. PFS includes deaths and thus can be a better correlate to overall survival. PFS assumes patient deaths are randomly related to tumor progression. However, in situations where the majority of deaths are unrelated to cancer, TTP can be an acceptable endpoint.

As an endpoint to support drug approval, PFS can reflect tumor growth and be assessed before the determination of a survival benefit. Its determination is not confounded by subsequent therapy. For a given sample size, the magnitude of effect on PFS can be larger than the effect on overall survival. However, the formal validation of PFS as a surrogate for survival for the many different malignancies that exist can be difficult. Data are sometimes insufficient to allow a robust evaluation of the correlation between effects on survival and PFS. Cancer trials are often small, and proven survival benefits of existing drugs are generally modest. The role of PFS as an endpoint to support licensing approval varies in different cancer settings. Whether an improvement in PFS represents a direct clinical benefit or a surrogate for clinical benefit depends on the magnitude of the effect and the risk-benefit of the new treatment compared to available therapies.

"Time-to-treatment failure" (TTF) is defined as a composite endpoint measuring time from randomization to discontinuation of treatment for any reason, including disease progression, treatment toxicity, and death. TTF is not recommended as a regulatory endpoint for drug approval. TTF does not adequately distinguish efficacy from these additional variables. A regulatory endpoint should clearly distinguish the efficacy of the drug from toxicity, patient or physician withdrawal, or patient intolerance.

The term "similar" or an equivalent thereof as used herein refers to resembling the reference or comparative term. In some embodiments, a numerical value is the value similar to a reference value if the difference between the numerical value and the reference value is within 5%, 10%, 15%, 20%, or 25% of the reference value. In some embodiments, a numerical value is similar to a reference value if the difference between the numerical value and the reference value is within 0.5% to 5%, 5% to 10%, 10% to 20%, or 15% to 25% of the reference value. In other embodiments, the term "similar" or an equivalent thereof is determined based on multiple features (or values) of a sample, for example, the expression levels of multiple genes of a patient. In yet other embodiments, the term "similar" or an equivalent thereof refers to belonging to the same group as determined by a classifier. In some embodiments, the term "similar" or an equivalent thereof is a relative term. For example, the similarity of a sample to a first reference sample is determined by comparing the sample with the first reference sample and a second reference sample, i.e., the sample is similar to the first reference sample as compared with the second reference sample.

The term "not similar," "differential," or an equivalent thereof as used herein refers to not resembling the reference or comparative term. In certain embodiments, a numerical value is the value not similar or differential to a reference value if the difference between the numerical value and the reference value is greater than 25% of the reference value. In other embodiments, the term "not similar," "differential," or an equivalent thereof is determined based on multiple features (or values) of a sample, for example, the expression levels of multiple genes of a patient. In yet other embodiments, the term "not similar," "differential," or an equivalent thereof refers to not belonging to the same group as determined by a classifier. In some embodiments, the term "not similar," "differential," or an equivalent thereof is a relative term. For example, a sample is not similar to a first reference sample is determined by comparing the sample with the first reference sample and a second reference sample, i.e., the sample is not similar to the first reference sample as compared with the second reference sample.

The term "predict" generally means to determine or tell in advance. When used to "predict" the effectiveness of a drug to treat a DLBCL patient, the term can mean, for example, the likelihood that the DLBCL patient will be responsive to the drug, as assessed prior to treatment with the drug or within a short period (e.g., within in hours, 1, 2, 3, 4 or more days, 1 week, or 2 weeks) of the treatment with the drug has begun.

As used herein the terms "polypeptide" and "protein" as used interchangeably herein, refer to a polymer of amino acids of three or more amino acids in a serial array, linked through peptide bonds. The term "polypeptide" includes proteins, protein fragments, protein analogues, oligopeptides and the like. The term polypeptide as used herein can also refer to a peptide. The amino acids making up the polypeptide may be naturally derived, or may be synthetic. The polypeptide can be purified from a biological sample.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition.

An mRNA from a patient sample can be "upregulated" when treated with a drug, as compared to a control. This upregulation can be, for example, an increase of about 5%, 10%, 20%, 30%, 40%, 50%, 60%, 70%, 90%, 100%, 200%, 300%, 500%, 1,000%, 5,000% or more of the comparative control mRNA level.

Alternatively, an mRNA can be "downregulated", or expressed at a lower level, in response to administration of certain drug or other therapies. A downregulated mRNA can be, for example, present at a level of about 99%, 95%, 90%, 80%, 70%, 60%, 50%, 40%, 30%, 20%, 10%, 1% or less of the comparative control mRNA level.

Similarly, a protein that is "upregulated" is generally increased upon a given treatment or condition. A protein that is "downregulated" generally refers to a decrease in the level of the protein in response to a given treatment or condition. In some situations, the protein level can remain unchanged upon a given treatment or condition.

The level of a polypeptide or protein biomarker from a patient sample can be increased when treated with a drug, as compared to a non-treated control. This increase can be about 5%, 10%, 20%, 30%, 40%, 50%, 60%, 70%, 90%, 100%, 200%, 300%, 500%, 1,000%, 5,000% or more of the comparative control protein level.

Alternatively, the level of a protein biomarker can be decreased in response to administration of certain drugs/compounds or other agents. This decrease can be, for example, present at a level of about 99%, 95%, 90%, 80%, 70%, 60%, 50%, 40%, 30%, 20%, 10%, 1% or less of the comparative control protein level.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. A nucleic acid also includes, in some aspects, a complementary DNA (cDNA). The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The terms "isolated" and "purified" refer to isolation of a substance (such as mRNA or protein) such that the substance comprises a substantial portion of the sample in which it resides, i.e. greater than the substance is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

The term "sample" as used herein relates to a material or mixture of materials, typically, although not necessarily, in fluid form, containing one or more elements of interest.

"Biological sample" as used herein refers to a sample obtained from a biological subject, including sample of biological tissue or fluid origin, obtained, reached, or collected in vivo or in situ. A biological sample also includes samples from a region of a patient containing precancerous or cancer cells or tissues. Such samples can be, but are not limited to, organs, tissues, fractions and cells isolated from a patient. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Other exemplary biological samples include whole blood, partially purified blood, PBMCs, tissue biopsies, and the like. In a specific embodiment, the biological sample is a tumor biopsy.

A "classifier" refers to a mathematical function that separates two or more groups, bodies or distributions of data according to the values with which each example of data is described, or an output of a function applied to those values in a manner that may be used to assign new data examples to one or more of the groups, bodies or distributions separated. The term "classifier" as used herein also includes regression or a function on data values that maps to a continuous target variable associated with the data examples, such as a function that relates gene expression values to PFS.

A biological marker or "biomarker" is a substance whose detection indicates a particular biological state, such as, for example, the responsiveness of a DLBCL patient to treatment with a drug. In some embodiments, biomarkers can either be measured individually, or several biomarkers can be measured simultaneously.

In some embodiments, a "biomarker" indicates a change in the level of mRNA expression that may correlate with responsiveness of a DLBCL patient to treatment with a drug. In some embodiments, the biomarker is a nucleic acid, such as an mRNA or cDNA.

In additional embodiments, a "biomarker" indicates a change in the level of polypeptide or protein expression that may correlate with the responsiveness of a DLBCL patient to treatment with a drug. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein the term "enantiomer," "isomer" or "stereoisomer" encompasses all enantiomerically/stereomerically pure and enantiomerically/stereomerically enriched compounds provided herein.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein the term "polymorph" means solid crystalline forms of a compound provided herein or complex thereof. Different polymorphs of the same compound can exhibit different physical, chemical and/or spectroscopic properties.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al. (1989) *Molecular Cloning, A Laboratory Manual* (2d ed.); D. N Glover, ed. (1985) *DNA Cloning*, Volumes I and II; M. J. Gait, ed. (1984) *Oligonucleotide Synthesis*; B. D. Hames & SJ. Higgins, eds. (1984) *Nucleic Acid Hybridization*; B. D. Hames & S. J. Higgins, eds. (1984) *Transcription and Translation*; R. I. Freshney, ed. (1986) *Animal Cell Culture, Immobilized Cells and Enzymes* (IRL Press, 1986); *Immunochemical Methods in Cell and Molecular Biology* (Academic Press, London); Scopes (1987) *Protein Purification: Principles and Practice* (2d ed.; Springer Verlag, N.Y.); and D. M. Weir and C. C. Blackwell, eds. (1986) *Handbook of Experimental Immunology*, Volumes I-IV.

5.2 Methods for Predicting Responsiveness of DLBCL Patients to Treatment Compounds The present application is based, in part, on the finding that the expression levels of several groups of genes (e.g., those listed in Tables 1, 2, and 3) correlate with a DLBCL patient's responsiveness to certain treatment compounds, such as lenalidomide or Compound A. Thus, in one aspect, provided herein are methods that can use the biomarkers and/or classifiers identified Tables 1, 2, and 3 below to predict responsiveness of a DLBCL patient to a drug, such as lenolidomide or Compound A.

TABLE 1

| Gene |
|---|
| ANXA4 |
| BACH2 |
| BIN2 |
| C7orf10 |
| CXCL14 |
| DAPL1 |
| FBXO32 |
| FCGR1B |
| FTX |
| GIMAP6 |
| IL18BP |
| KCNMB1 |
| KIAA1671 |
| LOC284837 |
| MPP6 |
| MZT1 |
| NFIC |
| ODF3B |
| OLFM1 |
| PPAT |
| RFESD |
| RPL22L1 |
| SERPING1 |
| TNC |
| TNFRSF17 |
| ZNF506 |

TABLE 2

| Gene |
|---|
| C10orf54 |
| C1RL |
| C20orf112 |
| C8orf4 |
| CCDC88C |
| CILP |
| CIRH1A |
| CLU |
| CPVL |
| CSF1R |
| CTSB |
| EPB41L3 |
| FBXO32 |
| IFI44 |
| LRP11 |
| MEGF6 |
| MEIS1 |
| PHACTR2 |
| PLAT |
| SERPING1 |
| SPC25 |
| THEMIS2 |
| TPSAB1 |
| ULK1 |
| XAF1 |
| ZNF215 |

TABLE 3

| Gene |
|---|
| BMS1P20 |
| MZB1 |
| TNFRSF17 |
| FKBP11 |
| IGLV1-44 |
| MS4A1 |
| BCL11A |
| MACROD2 |

TABLE 3-continued

| Gene |
|---|
| FAM129C |
| ALDH2 |
| KIAA1598 |
| TGFBI |
| TYMP |
| SAMD4A |
| GPX3 |
| A2M |
| CFB |
| FSTL1 |
| SLC27A3 |
| NRP1 |

In another aspect, the method for predicting responsiveness of a DLBCL patient to a drug comprises: (a) obtaining a first biological sample from a first patient having a DLBCL; (b) determining the level of expression of one, two, three, four, five or more of the genes identified in Table 1, 2 and/or 3; (c) comparing the level of expression of the one, two, three, four, five or more of the genes identified in Table 1, 2 and/or 3 in the first biological sample with the level of expression of the same genes in a second biological sample(s) from a second patient(s), wherein the second DLBCL patient(s) is not responsive to the drug, and wherein the differential expression of the one, two, three, four, five or more of the genes in the first biological sample relative to the level of expression of the one, two, three, four, five or more of the genes in the second biological sample(s) indicates that the DLBCL in the first patient will be responsive to treatment with the drug, wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof; or a pharmaceutically acceptable salt, solvate, hydrate, co-crystal, clathrate thereof; or a polymorph thereof.

In some embodiments, provided herein are methods for predicting responsiveness of a DLBCL patient to a drug comprising: (a) obtaining a first biological sample from a first patient having a DLBCL; (b) determining the level of expression of one, two, three, four, five or more of the genes identified in Table 1, 2, and/or 3; (c) comparing the level of expression of the one, two, three, four, five or more of the genes identified in Table 1, 2, and/or 3 in the first biological sample with the level of expression of the same genes in a second biological sample(s) from a second patient(s), wherein the second DLBCL patient(s) is responsive to the drug, and wherein the similar expression of the one, two, three, four, five or more of the genes in the first biological sample relative to the level of expression of the one, two, three, four, five or more of the genes in the second biological sample(s) indicates that the DLBCL in the first patient will be responsive to treatment with the drug, wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof, or a pharmaceutically acceptable salt, solvate, hydrate, co-crystal, clathrate thereof; or a polymorph thereof.

In another aspect, provided herein are methods for predicting responsiveness of a DLBCL patient to a drug comprising: (a) obtaining a first biological sample from a first DLBCL patient; (b) determining the expression of the genes or a certain subset of genes set forth in Table 1, 2, and/or 3, or any combination thereof, in the first biological sample;

and (c) comparing the gene expression profile of the genes or subset of genes in the first biological sample to (i) the gene expression profile of the genes or subset of genes in biological samples from DLBCL patients which are responsive to the drug and (ii) the gene expression of the genes or subset of genes in biological samples from DLBCL patients which are not responsive to the drug, wherein a gene expression profile for the genes or subset of genes in the first biological sample similar to the gene expression profile for the genes or subset of genes in biological samples from DLBCL patients which are responsive to the drug indicates that the first DLBCL patient will be responsive to treatment with the drug, and a gene expression profile for the genes or subset of genes in first biological sample similar to the gene expression profile for the genes or subset of genes in biological samples from DLBCL patients which are not responsive to the drug indicates that the first DLBCL patient will not be responsive to treatment with the drug, wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof; or a pharmaceutically acceptable salt, solvate, hydrate, co-crystal, clathrate thereof; or a polymorph thereof. In some embodiments, the subset(s) of genes are a subset(s) of those genes in Table 1, a subset(s) of those genes in Table 2, and/or a subset(s) of those genes in Table 3, or any combination thereof.

In some embodiments, expression levels of multiple genes (biomarkers) provided herein are used to predict a patient's response to the compound provided herein. When expression levels of multiple genes (biomarkers) are used to predict a patient's response to a treatment with the compound provided herein, e.g., lenalidomide and Compound A, any classifier that classifies based on two or more features can be used in the present disclosure. For example, in some embodiments, a population of DLBCL patients that have received a treatment with the compound provide herein (e.g., lenalidomide or Compound A) are divided into two groups based on their responsivienss to the compound treatment, i.e., responsive patient group and non-responsive patient group. The expression levels of two or more genes provided herein (e.g., those listed in Tables 1-3) for each patient in the population are analyzed using a classifier and a score can be generated. A reference score or a threshold score can be generated based on the scores of the responsive patients and the scores of non-responsive patients. Such reference score can be used to predict a patient's responsiveness to the compound based on the expression levels of the genes of this patient.

In some embodiments, the methods provided herein further comprise (a) generating a score of the sample based on the expression levels of the genes or a subset thereof provided herein in the sample; and (b) determining the probability of the subject being responsive to the compound provided herein by comparing the score of the sample to a reference score.

In some embodiments, the methods provided herein further comprise: (a) determining the expression levels of the genes or a subset thereof provided herein in a biological sample from a population of subjects that previously have been administered with the compound provided herein, (b) generating a score for the expression levels of the genes or a subset thereof provided herein for each subject of the population; (c) differentiating the subjects that are responsive to the compound provided herein from those subjects that are not responsive to the compound provided herein; and (d) determining responsiveness to the compound provided herein based on the scores for the subjects that are responsive to the compound and those subjects that are not responsive to the compound.

In other embodiments, the methods provided herein further comprise: (a) determining the expression levels of the genes or a subset thereof provided herein in a biological sample from a population of subjects that previously have been administered with the compound, (b) generating a score for the expression levels of the genes or a subset thereof provided herein for each subject of the population; (c) differentiating the subjects that are responsive to the compound provided herein from those subjects that are not responsive to compound provided herein; and (d) generating a reference score that is predictive of the responsiveness of a subject to the compound provided herein using a model based on the scores for the subjects that are responsive to the compound and those subjects that are not responsive to the compound.

In another aspect, provided herein are methods for predicting responsiveness of a DLBCL patient to a drug comprising: (a) obtaining a first biological sample from a first DLBCL patient; (b) determining the expression of the genes or a certain subset of genes set forth in Table 1, 2 and/or 3, or any combination thereof, in the first biological sample and generating a score based on the expression of the genes or subset of genes, (c) comparing the score to a reference score, wherein a score similar to a reference score indicates that the patient will be responsive to treatment with the drug. In specific embodiments, the reference score is based on the expression of the same genes or subset of genes in a population of DLBCL patients responsive to the drug. In a specific embodiment, the drug is a compound disclosed herein.

In another aspect, provided herein are methods for predicting responsiveness of a DLBCL patient with a drug comprising: (a) obtaining a first biological sample from a first DLBCL patient; (b) determining the expression of the genes or a certain subset of genes set forth in Table 1, 2 and/or 3, or any combination thereof, in the first biological sample and generating a score based on the expression of the genes or subset of genes, (c) comparing the score to a first reference score and a second reference score, wherein a score similar to the first reference score indicates that the patient will be responsive to the treatment with the drug. In specific embodiments, the first reference score is based on the expression of the same genes or subset of genes in a population of DLBCL patients responsive to the drug and the second reference score is based on the expression of the same genes or subset of genes in a population of DLBCL patients not responsive to the drug. In a specific embodiment, the drug is a compound disclosed herein.

In some embodiments, the determining step of the methods described herein comprising determining the expression of the genes or a certain subset of genes set forth in Table 1 in the first biological sample. For example, in certain embodiments, the subset of genes can include 2, 3, 4, 5, 6, 7, 8, 9, 10, 11, 12, 13, 14, 15, 16, 20, 25 or more genes listed in Table 1. In another embodiment, the subset of genes can include between 2 to 20 genes, or alternatively between 3 to 20 genes, alternatively between 5 to 15 genes, or alternatively 10 to 20 genes listed in Table 1. In some embodiments, the determining step of the methods described herein comprises determining the expression of one or more genes selected from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, and ZNF506.

In some embodiments, the determining step of the methods described herein comprising determining the expression of the genes or a certain subset of genes set forth in Table 2 in the first biological sample. For example, in certain embodiments, the subset of genes can include 2, 3, 4, 5, 6, 7, 8, 9, 10, 11, 12, 13, 14, 15, 16, 20, 25 or more genes listed in Table 2. In another embodiment, the subset of genes can include between 2 to 20 genes, or alternatively between 3 to 20 genes, alternatively between 5 to 15 genes, or alternatively 10 to 20 genes listed in Table 2. In some embodiments, the determining step of the methods described herein comprises determining the expression of one or more genes selected from the group consisting of C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, and ZNF215.

In some embodiments, the determining step of the methods described herein comprising determining the expression of the genes or a certain subset of genes set forth in Table 3 in the first biological sample. For example, in certain embodiments, the subset of genes can include 2, 3, 4, 5, 6, 7, 8, 9, 10, 11, 12, 13, 14, 15, 16, 19 or more genes listed in Table 3. In another embodiment, the subset of genes can include between 2 to 19 genes, or alternatively between 3 to 19 genes, alternatively between 5 to 15 genes, or alternatively 10 to 19 genes listed in Table 3. In some embodiments, the determining step of the methods described herein comprises determining the expression of one or more genes selected from the group consisting of BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1. In some embodiments, the subset of genes includes BMS1P20, MZB1, TNFRSF17, FKBP11, and IGLV1-44. In other embodiments, the subset of genes includes MS4A1, BCL11A, MACROD2, and FAM129C. In yet other embodiments, the subset of genes includes ALDH2, KIAA1598, TGFBI, TYMP, and SAMD4A. In yet other embodiments, the subset of genes includes GPX3, A2M, CFB, FSTL1, SLC27A3, and NRP1.

In some embodiments, the determining step of the methods described herein comprising determining the expression of the genes or a certain subset of genes set forth in a combination of Tables 1, 2, and 3 in the first biological sample. For example, in certain embodiments, the subset of genes can include 2, 3, 4, 5, 6, 7, 8, 9, 10, 11, 12, 13, 14, 15, 16, 20, 25, 30, 35, 40, 50, 60, 70 or more genes listed in Tables 1, 2, and 3. In another embodiment, the subset of genes can include between 2 to 71 genes, or alternatively between 2 to 20 genes, or alternatively between 3 to 20 genes, alternatively between 5 to 15 genes, or alternatively 10 to 20 genes listed in Tables 1, 2, and 3. In some embodiments, the determining step of the methods described herein comprises determining the expression of one or more genes (biomarkers) selected from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, ZNF506, C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, ZNF215, BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1.

In one embodiment, the biomarker is ANXA4. In another embodiment, the biomarker is BACH2. In another embodiment, the biomarker is BIN2. In another embodiment, the biomarker is C7orf10. In another embodiment, the biomarker is CXCL14. In yet another embodiment, the biomarker is DAPL1. In yet another embodiment, the biomarker is FBXO32. In yet another embodiment, the biomarker is FCGR1B. In yet another embodiment, the biomarker is FTX. In yet another embodiment, the biomarker is GIMAP6. In yet another embodiment, the biomarker is IL18BP. In yet another embodiment, the biomarker is KCNMB1. In yet another embodiment, the biomarker is KIAA1671. In yet another embodiment, the biomarker is LOC284837. In yet another embodiment, the biomarker is MPP6. In yet another embodiment, the biomarker is MZT1. In yet another embodiment, the biomarker is NFIC. In yet another embodiment, the biomarker is ODF3B. In yet another embodiment, the biomarker is OLFM1. In yet another embodiment, the biomarker is PPAT. In yet another embodiment, the biomarker is RFESD. In yet another embodiment, the biomarker is RPL22L1. In yet another embodiment, the biomarker is SERPING1. In yet another embodiment, the biomarker is TNC. In yet another embodiment, the biomarker is TNFRSF17. In yet another embodiment, the biomarker is ZNF506. In yet another embodiment, the biomarker is C10orf54. In yet another embodiment, the biomarker is C1RL. In yet another embodiment, the biomarker is C20orf112. In yet another embodiment, the biomarker is C8orf4. In yet another embodiment, the biomarker is CCDC88C. In yet another embodiment, the biomarker is CILP. In yet another embodiment, the biomarker is CIRH1A. In yet another embodiment, the biomarker is CLU. In yet another embodiment, the biomarker is CPVL. In yet another embodiment, the biomarker is CSF1R. In yet another embodiment, the biomarker is CTSB. In yet another embodiment, the biomarker is EPB41L3. In yet another embodiment, the biomarker is FBXO32. In yet another embodiment, the biomarker is IFI44. In yet another embodiment, the biomarker is LRP11. In yet another embodiment, the biomarker is MEGF6. In yet another embodiment, the biomarker is MEIS1. In yet another embodiment, the biomarker is PHACTR2. In yet another embodiment, the biomarker is PLAT. In yet another embodiment, the biomarker is SERPING1. In yet another embodiment, the biomarker is SPC25. In yet another embodiment, the biomarker is THEMIS2. In yet another embodiment, the biomarker is TPSAB1. In yet another embodiment, the biomarker is ULK1. In yet another embodiment, the biomarker is XAF1. In yet another embodiment, the biomarker is ZNF215. In yet another embodiment, the biomarker is BMS1P20. In yet another embodiment, the biomarker is MZB1. In yet another embodiment, the biomarker is TNFRSF17. In yet another embodiment, the biomarker is FKBP11. In yet another embodiment, the biomarker is IGLV1-44. In yet another embodiment, the biomarker is MS4A1. In yet another embodiment, the biomarker is BCL11A. In yet another embodiment, the biomarker is MACROD2. In yet another embodiment, the biomarker is FAM129C. In yet another embodiment, the biomarker is ALDH2. In yet another embodiment, the biomarker is KIAA1598. In yet another embodiment, the biomarker is TGFBI. In yet another embodiment, the biomarker is TYMP.

In yet another embodiment, the biomarker is SAMD4A. In yet another embodiment, the biomarker is GPX3. In yet another embodiment, the biomarker is A2M. In yet another embodiment, the biomarker is CFB. In yet another embodiment, the biomarker is FSTL1. In yet another embodiment, the biomarker is SLC27A3. In yet another embodiment, the biomarker is NRP1.

In certain embodiments, in accordance with the methods described herein, the gene expression profile or data is derived from the same type of biological sample. In other words, the biological sample used to generate each gene expression profile or data referenced in the methods is the same type of biological sample. In some embodiments, the biological samples are tumor biopsy samples.

In some embodiments, the determining step of the methods described herein comprises detecting the presence and/or amount of a complex in the biological sample, wherein the presence and/or amount of the complex indicates the expression level of the genes. The complex detected in the methods described herein can be a hybridization complex and in some embodiments, the hybridization complex is attached to a solid support. In further embodiments, the complex is detectably labeled.

In some embodiments, the determining step of the methods described herein comprises detecting the presence and/or amount of a reaction product in the biological sample, wherein the presence and/or amount of the reaction product indicates the expression level of the genes in each subset of genes. In further embodiments, the reaction product is detectably labeled.

In some embodiments, the expression of the genes or biomarkers provided herein is determined by determining the protein levels of the genes or biomarkers. In other embodiments, the expression of the genes or biomarkers provided herein is determined by determining the mRNA levels of the genes or biomarkers. In yet other embodiments, the expression of the genes provided herein is determined by determining the levels of cDNA generated using the mRNA of a gene or biomarker. Accordingly, the upregulation or downregulation of the nucleic acids (e.g., mRNA or cDNA) or proteins of the genes provided herein (e.g., those listed in Tables 1-3) can be used to predict a DLBCL patient's response to a compound treatment.

In some embodiments, a statistical analysis or other analysis is performed on data from the assay utilized to measure an RNA transcript or protein. In certain specific embodiments, the p value of those RNA transcripts or proteins differentially expressed is 0.1, 0.5, 0.4, 0.3, 0.2, 0.01, 0.05, 0.001, or 0.0001. In some embodiments, the p-value provided herein is the output of a statistical test of difference between two or more groups of values or data examples. In specific embodiments, a false discovery rate (FDR) of 10%, 9%, 8%, 7%, 6%, 5%, 4%, 3%, 2% or less is selected. FDR correction and associated thresholds are commonly applied to correct p-values for multiple hypothesis testing, i.e. applying the same test or comparison to many groups of values before seeking to assign statistical significance to a subset of the differences observed. In some embodiments, hypothesis testing for difference may also be applied to output of a functional transformation of assay output. In some embodiments, additional processes other than tests of difference can be used to classify or predict drug response from assay output.

In some embodiments, the methods described herein include predicting responsiveness of a DLBCL patient, wherein the DLBCL is refractory in the DLBCL patient.

In some embodiments, the methods described herein include predicting responsiveness of a DLBCL patient, wherein the DLBCL is relapsed in the DLBCL patient.

In some embodiments, the methods described herein include predicting responsiveness of a DLBCL patient, wherein the DLBCL is a germinal center B-cell-like subtype in the DLBCL patient.

In some embodiments, the methods described herein include predicting responsiveness of a DLBCL patient, wherein the DLBCL is activated B-cell like in the DLBCL patient.

In some embodiments, the methods described herein include predicting responsiveness of a DLBCL patient, wherein the DLBCL is Type III (also referred to as "unclassified") in the DLBCL patient.

In some embodiments, the methods described herein include determining the gene expression profile of a subset(s) of genes in DLBCL patients that have taken the drug prior to treatment with the drug, wherein each subset of genes relates to a tumor biopsy composition.

5.2.1 Examples of Application of the Biomarkers to Predict Responsiveness of DLBCL Patients to Lenalidomide and Compound A Tables 1, 2, and 3 provide lists of genes that can be used as biomarkers to predict the responsiveness of a DLBCL patient to a drug. In certain embodiments, a combination of 1, 2, 3, 4, 5, 6, 7, 8, 9, 10, 11, 12, 13, 14, 15, 16, 20 or more genes listed in Table 1, Table 2 or Table 3, or any combination thereof, can be sued as biomarkers to predict the responsiveness of a DLBCL patient to a drug. In some embodiments, 1 to 5, 5 to 10, 10 to 15, 15 to 20, or 20 to 25 genes in Table 1, Table 2 or Table 3 can be sued as biomarkers to predict the responsiveness of a DLBCL patient to a drug.

In certain embodiments, a combination of 1, 2, 3, 4, 5, 6, 7, 8, 9, 10, 11, 12, 13, 14, 15, 16, 20, 25 or more genes listed in Table 1; 1, 2, 3, 4, 5, 6, 7, 8, 9, 10, 11, 12, 13, 14, 15, 16, 20, 25 or more genes listed in Table 2; and 1, 2, 3, 4, 5, 6, 7, 8, 9, 10, 11, 12, 13, 14, 15, 16, 19 or more genes listed in Table 3 can be used as biomarkers to predict the responsiveness of a DLBCL patient to a drug. In some embodiments, a combination of 1 to 5, 5 to 10, 10 to 15, 15 to 20, 20 to 25 genes in Table 1; 1 to 5, 5 to 10, 10 to 15, 15 to 20, 20 to 25 genes in Table 2; and 1 to 5, 5 to 10, 10 to 15, 15 to 20 genes in Table 3 are used as biomarkers to predict the responsiveness of a DLBCL patient to a drug.

In some embodiments, a combination of 1, 2, 3, 4, 5, 6, 7, 8, 9, 10, 11, 12, 13, 14, 15, 16, 20, 25 or more genes listed in Table 1 and 1, 2, 3, 4, 5, 6, 7, 8, 9, 10, 11, 12, 13, 14, 15, 16, 20, 25 or more genes listed in Table 2 are used as biomarkers to predict the responsiveness of a DLBCL patient to a drug. In some embodiments, a combination of 1 to 5, 5 to 10, 10 to 15, 15 to 20, 20 to 25 genes in Table 1 and 1 to 5, 5 to 10, 10 to 15, 15 to 20, 20 to 25 genes in Table 2 are used as biomarkers to predict the responsiveness of a DLBCL patient to a drug.

In other embodiments, a combination of 1, 2, 3, 4, 5, 6, 7, 8, 9, 10, 11, 12, 13, 14, 15, 16, 20, 25 or more genes listed in Table 1 and 1, 2, 3, 4, 5, 6, 7, 8, 9, 10, 11, 12, 13, 14, 15, 16, 19 or more genes listed in Table 3 can be used as biomarkers to predict the responsiveness of a DLBCL patient to a drug. In other embodiments, a combination of 1 to 5, 5 to 10, 10 to 15, 15 to 20, 20 to 25 genes in Table 1 and 1 to 5, 5 to 10, 10 to 15, 15 to 20 genes in Table 3 are used as biomarkers to predict the responsiveness of a DLBCL patient to a drug.

In yet other embodiments, a combination of 1, 2, 3, 4, 5, 6, 7, 8, 9, 10, 11, 12, 13, 14, 15, 16, 20, 25 or more genes listed in Table 2 and 1, 2, 3, 4, 5, 6, 7, 8, 9, 10, 11, 12, 13, 14, 15, 16, 19 or more genes listed in Table 3 can be used as biomarkers to predict the responsiveness of a DLBCL patient to a drug. In yet other embodiments, a combination of 1 to 5, 5 to 10, 10 to 15, 15 to 20, 20 to 25 genes in Table 2 and 1 to 5, 5 to 10, 10 to 15, 15 to 20 genes in Table 3 are used as biomarkers to predict the responsiveness of a DLBCL patient to a drug.

Additionally, in some embodiments, all of the genes listed in Table 1, Table 2 and/or Table 3 can be used as biomarkers to predict the responsiveness of a DLBCL patient to a drug.

The biomarkers in Table 1, Table 2, and/or Table 3 can be used by a health professional in combination with other factors to determine whether or not to treat the DLBCL patient with the drug, e.g., lenalidomide or Compound A.

Figure 2:
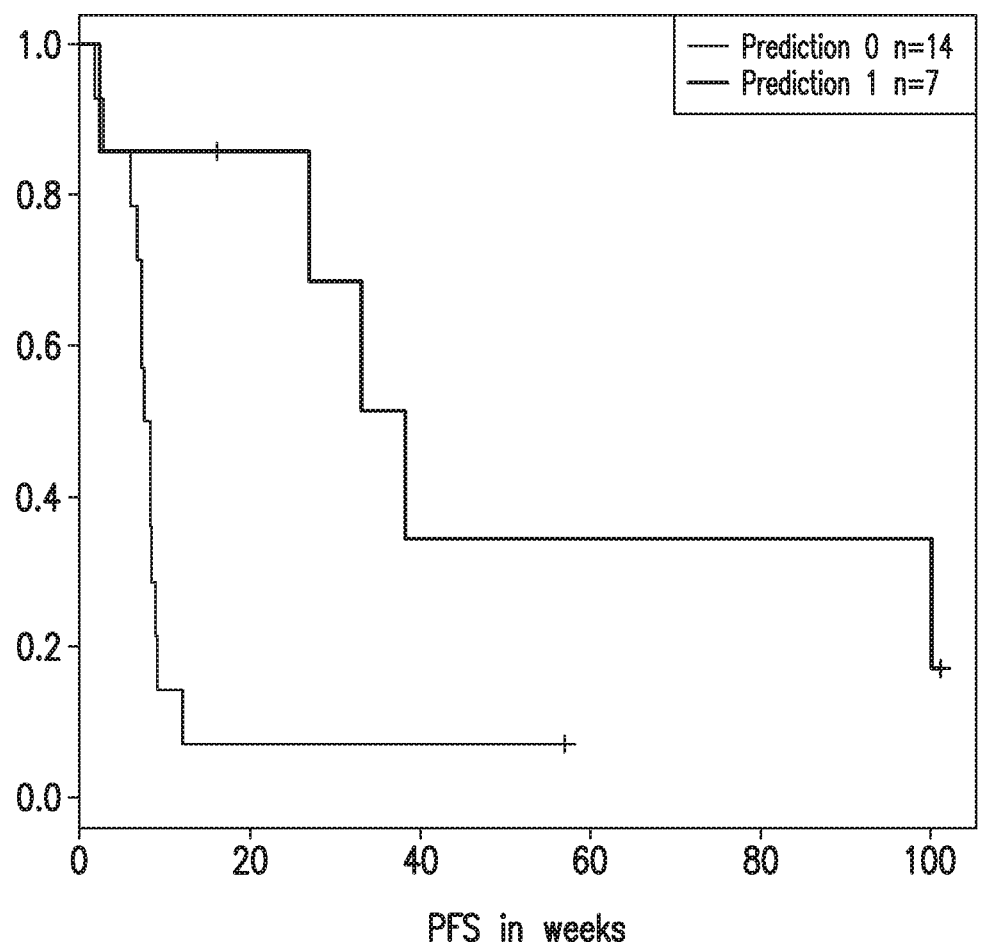

For example, a computational decision function was applied to gene expression values for gene subsets in Table 1 and Table 2 to predict the positive/negative outcome sub-group membership of gene expression profiles from the lenalidomide arm of Celgene trial REV-DLC-001 (see clinical trials website; clinical trial identifier NCT 01197560) in relapsed/refractory DLBCL. FIG. 1 displays a Kaplan-Meier survival plot of differential Investigator-determined progression-free survival (PFS) for patients in the lenalidomide-arm of REV-DLC-001, stratified according to the classifier prediction for Table 1. FIG. 2 displays a Kaplan-Meier survival plot of differential Investigator-determined PFS for patients in the lenalidomide-arm of REV-DLC-001, stratified according to the classifier prediction for Table 2. Cox regression models and Kaplan-Meier curves were performed using the R package survival (Terry M. Therneau, and Patricia M. Grambsch (2000). Modeling Survival Data: Extending the Cox Model (New York: Springer).

Predictions made by the classifier developed across gene expression profiles from the lenalidomide-arm of REV-DLC-001 for the gene subset described in Table 1 and Table 2 are listed in Table 4 and Table 5, respectively.

TABLE 4

Predictions Using the Genes of Table 1 by Linear SVM-RFE Classifier
Columns (from left to right): Patient ID; Predicted outcome class (+1 for positive, −1 otherwise); IRAC Best response category; IRAC-derived PFS; IRAC-derived PFS censor events; Investigator-derived PFS; Investigator-derived PFS censor events; Predicted cell-of-origin (Wright et al., PNAS USA, 100, 9991-9996 (2003)).

| Patient | Prediction | IRAC | IRAC_PFS | censor_IRACPFS | INV_PFS | censor_INVPFS | predCOO |
|---|---|---|---|---|---|---|---|
| 21002 | −1 | PD | 4.714286 | 0 | 6.714286 | 0 | Unclass |
| 21009 | −1 | PR | 16.142857 | 1 | 16.142857 | 1 | GCB |
| 1001001 | 1 | CR | 82 | 0 | 100.142857 | 0 | ABC |
| 1001005 | −1 | PD | 8.857143 | 0 | 8.857143 | 0 | GCB |
| 1051001 | 1 | PR | 25.142857 | 0 | 33.142857 | 0 | GCB |
| 1061003 | −1 | Death | 10.142857 | 0 | 2.857143 | 0 | GCB |
| 1511003 | 1 | Death | 2.285714 | 0 | 2.285714 | 0 | ABC |
| 1511004 | 1 | SD | 27 | 0 | 27 | 0 | GCB |
| 2021004 | −1 | PD | 8.285714 | 0 | 8.285714 | 0 | GCB |
| 2021005 | −1 | PD | 9.142857 | 0 | 9.142857 | 0 | ABC |
| 3051001 | 1 | CR | 34.285714 | 0 | 38.285714 | 0 | GCB |
| 4011002 | −1 | Death | 24.857143 | 0 | 1.714286 | 0 | GCB |
| 4011004 | −1 | Death | 5.857143 | 0 | 5.857143 | 0 | GCB |
| 4051001 | −1 | PD | 7.285714 | 0 | 7.285714 | 0 | Unclass |
| 6031002 | −1 | PD | 8.285714 | 0 | 8.285714 | 0 | ABC |
| 6031003 | −1 | CR | 57.142857 | 1 | 57.142857 | 1 | ABC |
| 6041002 | 1 | CR | 101.285714 | 1 | 101.285714 | 1 | ABC |
| 6051001 | −1 | SD | 21.714286 | 0 | 12.142857 | 0 | GCB |
| 6071002 | −1 | SD | 7.571429 | 1 | 7.571429 | 0 | ABC |
| 6601001 | −1 | SD | 7.714286 | 0 | 8.428571 | 0 | GCB |
| 6601002 | −1 | PD | 7.285714 | 0 | 7.285714 | 0 | ABC |

TABLE 5

Predictions Using the Genes of Table 2 by Linear SVM-RFE Classifier
Columns (from left-to right): Patient ID; Predicted outcome class (+1 for positive, −1 otherwise); IRAC Best response category; IRAC-derived PFS; IRAC-derived PFS censor events; Investigator-derived PFS; Investigator-derived PFS censor events; Predicted cell-of-origin (Wright et al., PNAS USA, 100, 9991-9996 (2003)).

| Patient | Prediction | IRAC | IRAC_PFS | censor_IRACPFS | INV_PFS | censor_INVPFS | predCOO |
|---|---|---|---|---|---|---|---|
| 21002 | −1 | PD | 4.714286 | 0 | 6.714286 | 0 | Unclass |
| 21009 | 1 | PR | 16.142857 | 1 | 16.142857 | 1 | GCB |
| 1001001 | 1 | CR | 82 | 0 | 100.142857 | 0 | ABC |
| 1001005 | −1 | PD | 8.857143 | 0 | 8.857143 | 0 | GCB |
| 1051001 | 1 | PR | 25.142857 | 0 | 33.142857 | 0 | GCB |
| 1061003 | −1 | Death | 10.142857 | 0 | 2.857143 | 0 | GCB |
| 1511003 | 1 | Death | 2.285714 | 0 | 2.285714 | 0 | ABC |
| 1511004 | 1 | SD | 27 | 0 | 27 | 0 | GCB |
| 2021004 | −1 | PD | 8.285714 | 0 | 8.285714 | 0 | GCB |
| 2021005 | −1 | PD | 9.142857 | 0 | 9.142857 | 0 | ABC |

TABLE 5-continued

Predictions Using the Genes of Table 2 by Linear SVM-RFE Classifier
Columns (from left-to right): Patient ID; Predicted outcome class (+1 for positive, −1
otherwise); IRAC Best response category; IRAC-derived PFS; IRAC-derived PFS censor
events; Investigator-derived PFS; Investigator-derived PFS censor events; Predicted cell-of-
origin (Wright et al., PNAS USA, 100, 9991-9996 (2003)).

| Patient | Prediction | IRAC | IRAC_PFS | censor_IRACPFS | INV_PFS | censor_INVPFS | predCOO |
|---|---|---|---|---|---|---|---|
| 3051001 | 1 | CR | 34.285714 | 0 | 38.285714 | 0 | GCB |
| 4011002 | −1 | Death | 24.857143 | 0 | 1.714286 | 0 | GCB |
| 4011004 | −1 | Death | 5.857143 | 0 | 5.857143 | 0 | GCB |
| 4051001 | −1 | PD | 7.285714 | 0 | 7.285714 | 0 | Unclass |
| 6031002 | −1 | PD | 8.285714 | 0 | 8.285714 | 0 | ABC |
| 6031003 | −1 | CR | 57.142857 | 1 | 57.142857 | 1 | ABC |
| 6041002 | 1 | CR | 101.285714 | 1 | 101.285714 | 1 | ABC |
| 6051001 | −1 | SD | 21.714286 | 0 | 12.142857 | 0 | GCB |
| 6071002 | −1 | SD | 7.571429 | 1 | 7.571429 | 0 | ABC |
| 6601001 | −1 | SD | 7.714286 | 0 | 8.428571 | 0 | GCB |
| 6601002 | −1 | PD | 7.285714 | 0 | 7.285714 | 0 | ABC |

The results shown in FIGS. 1-2 and Tables 4-5 demonstrate that the classifier solutions based on the genes of Table 1 and Table 2 are predictive for responsiveness of DLBCL patients to lenalidomide.

In another exemplary study, a computational decision function was applied to gene expression values for the 26 genes in Table 2 to predict the positive/negative outcome sub-group membership of relapsed or refractory DLBCL patients for responsiveness to Compound A treatment alone or in combination with other agents.

The response to Compound A treatment of each of a group of relapsed or refractory DLBCL patients was predicated based on the gene expression levels of 26 genes of Table 2, and the group of patients were classified into two populations—the population predicted to be responsive to Compound A treatment (26 genes positive population) and the other population predicted to be not responsive to Compound A (26 genes negative population).

The expression levels of the 26 genes were measured as follows: DLBCL lymph-node biopsies were formalin fixed and paraffin embedded. Nucleic acids obtained from the tissues were extracted using the Roche High Pure FPPET kit, according to the manufacturer's instructions. The RNA was quantitated using spectrophotometry (NanoDrop, Thermo Science, DE). Gene expression on approximately 200 nanograms of RNA was used to determine gene expression levels by means of NanoString technology (NanoString Technologies, WA). The total RNA was hybridized to the custom codesets at 65° C. overnight. The reaction was processed on the nCounter™ Prep Station and gene expression data was then acquired on the nCounter™ Digital Analyzer.

Figure 3:
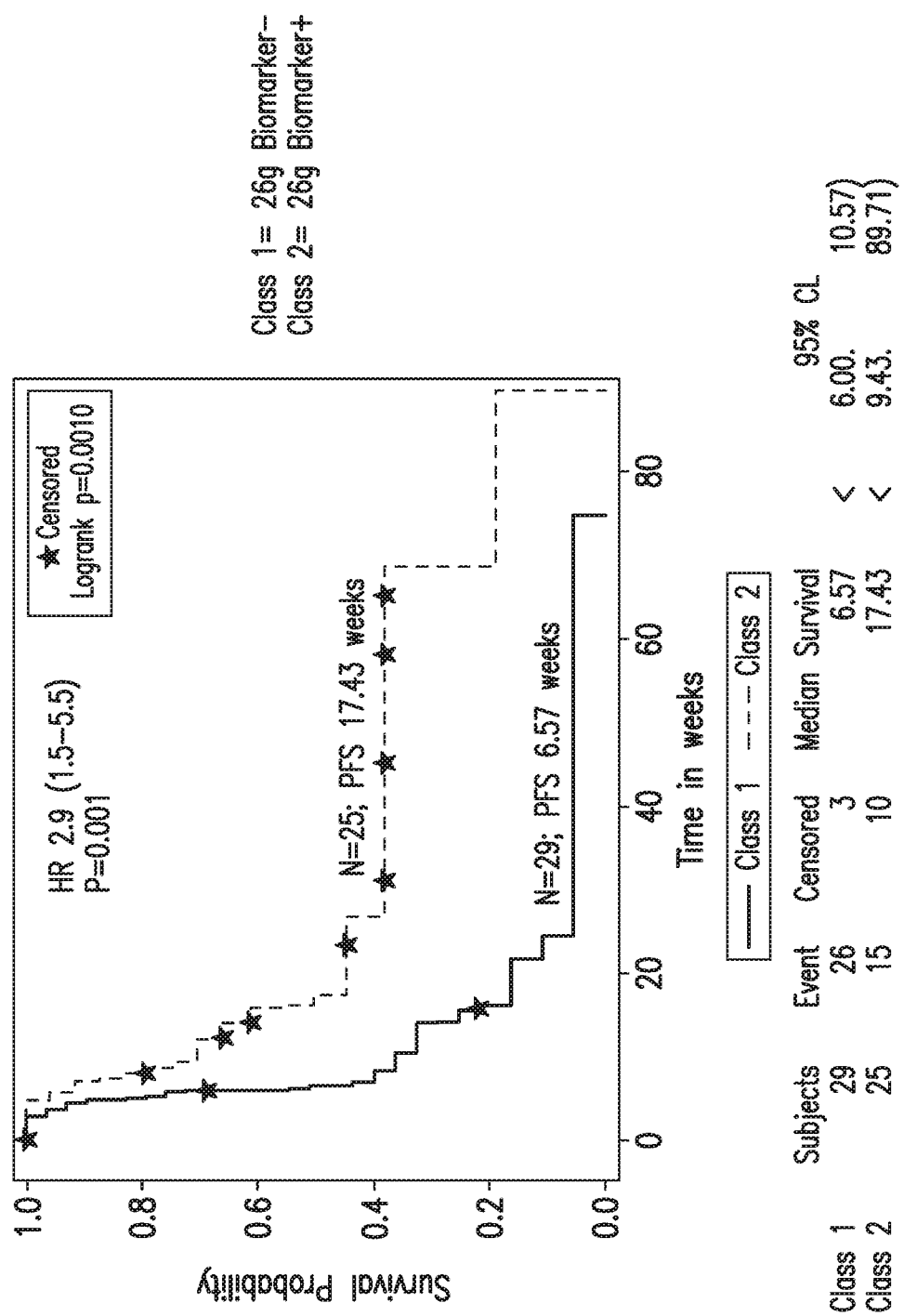
FIG. 3 shows the patients' response to Compound A treatment as measured by PFS.

Then, the patients' response to Compound A treatment were measured by progression free survival (PFS). The results are shown in FIG. 3, and as shown, that there is a significant benefit, as measured by PFS, of 26 gene positive population (upper line) as compared to 26 genes negative population (lower line) (PFS 17.43 weeks in 26 genes positive population versus PFS 6.57 weeks in 26 genes negative population).

Figure 4:
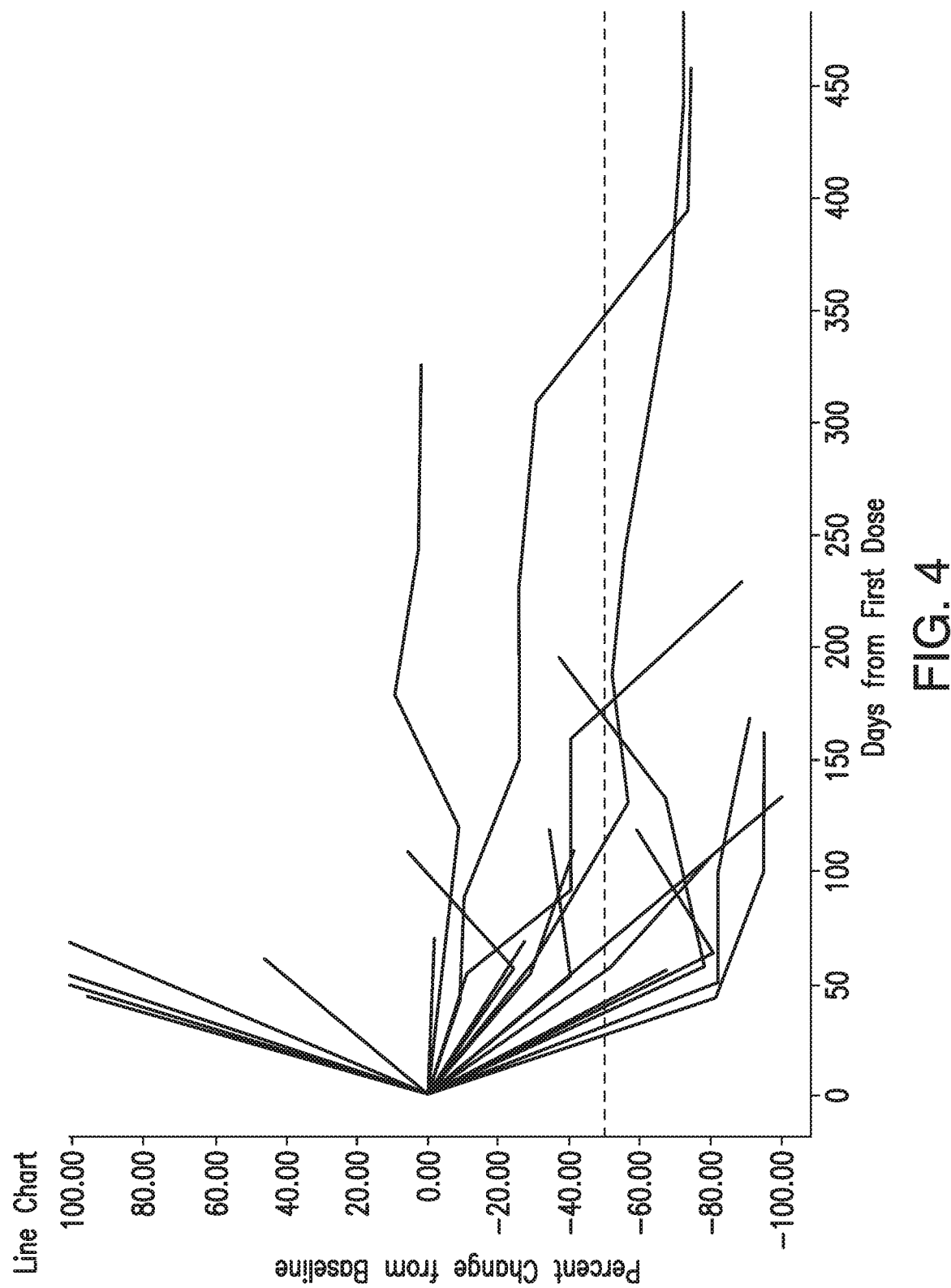
FIG. 4 shows the measurement of tumors from those patients in the 26 genes positive population in response to Compound A treatment.
Figure 5:
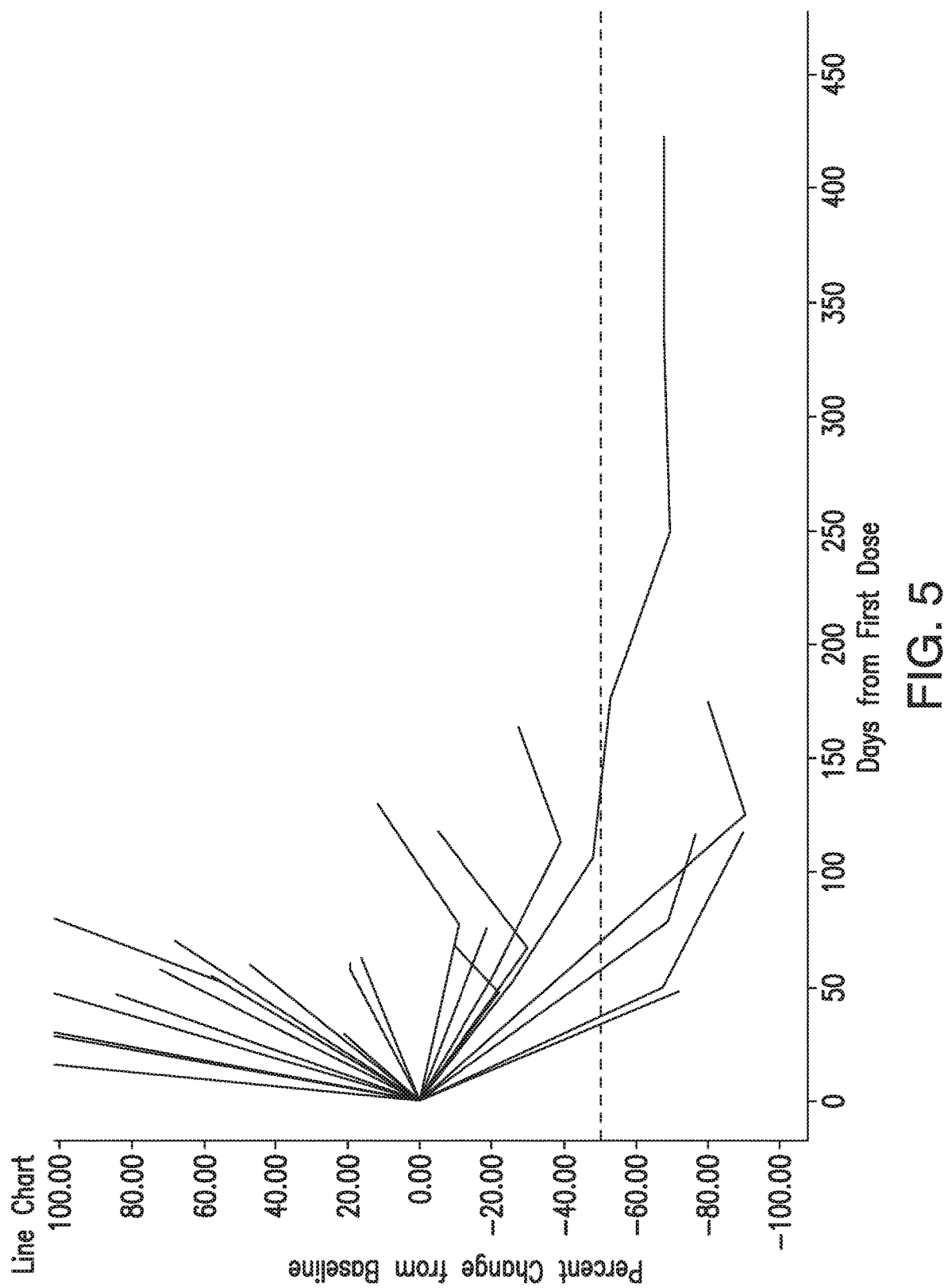
FIG. 5 shows the measurement of tumors from those patients in the 26 genes negative population in response to Compound A treatment.

The tumor of each patient was measured and the results demonstrated that the majority of those patients in the 26 genes positive population (see FIG. 4) obtained clinical response of greater than 50% decrease in tumor size and/or have stable disease. In contrast, the majority of the patients in the 26 genes negative population (see FIG. 5) experienced rapid progression or short responses to Compound A. The progression PFS at 6 months for the 26 genes positive population was 44.6% as compared to the 26 genes negative population (at 5.4%).

Figure 6:
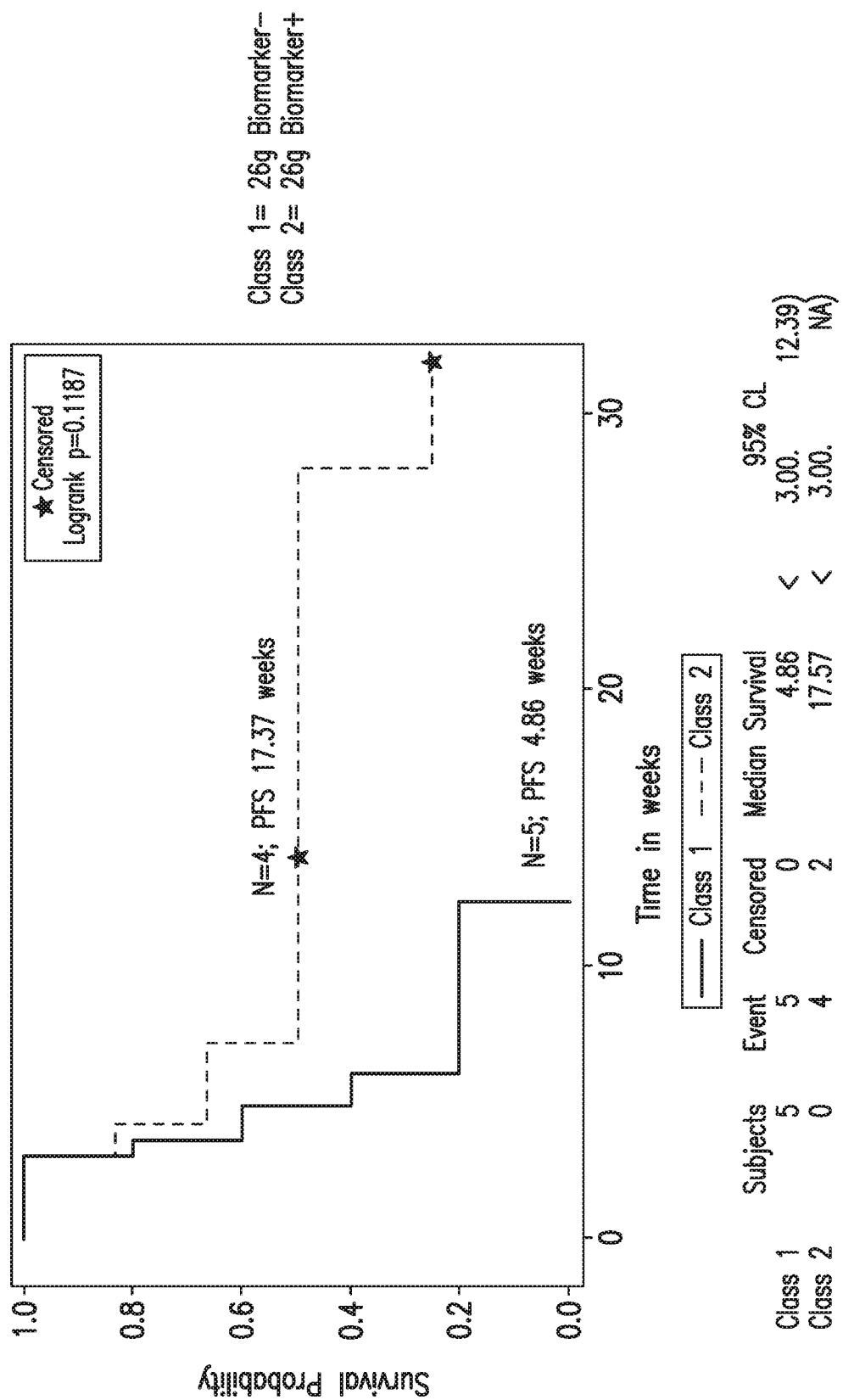
FIG. 6 shows the patients' response to the treatment with Compound A and Rituximab as measured by PFS.

The predictive performance of the classifier based on the 26 genes was also evaluated in patients receiving Compound A in combination with Rituximab. The results are shown in FIG. 6. As shown, that there is also a significant benefit, as measured by PFS, of 26 gene positive population (upper line) as compared to 26 genes negative population (lower line) (PFS 17.37 weeks in 26 genes positive population versus PFS 4.86 weeks in 26 genes negative population).

Figure 7:
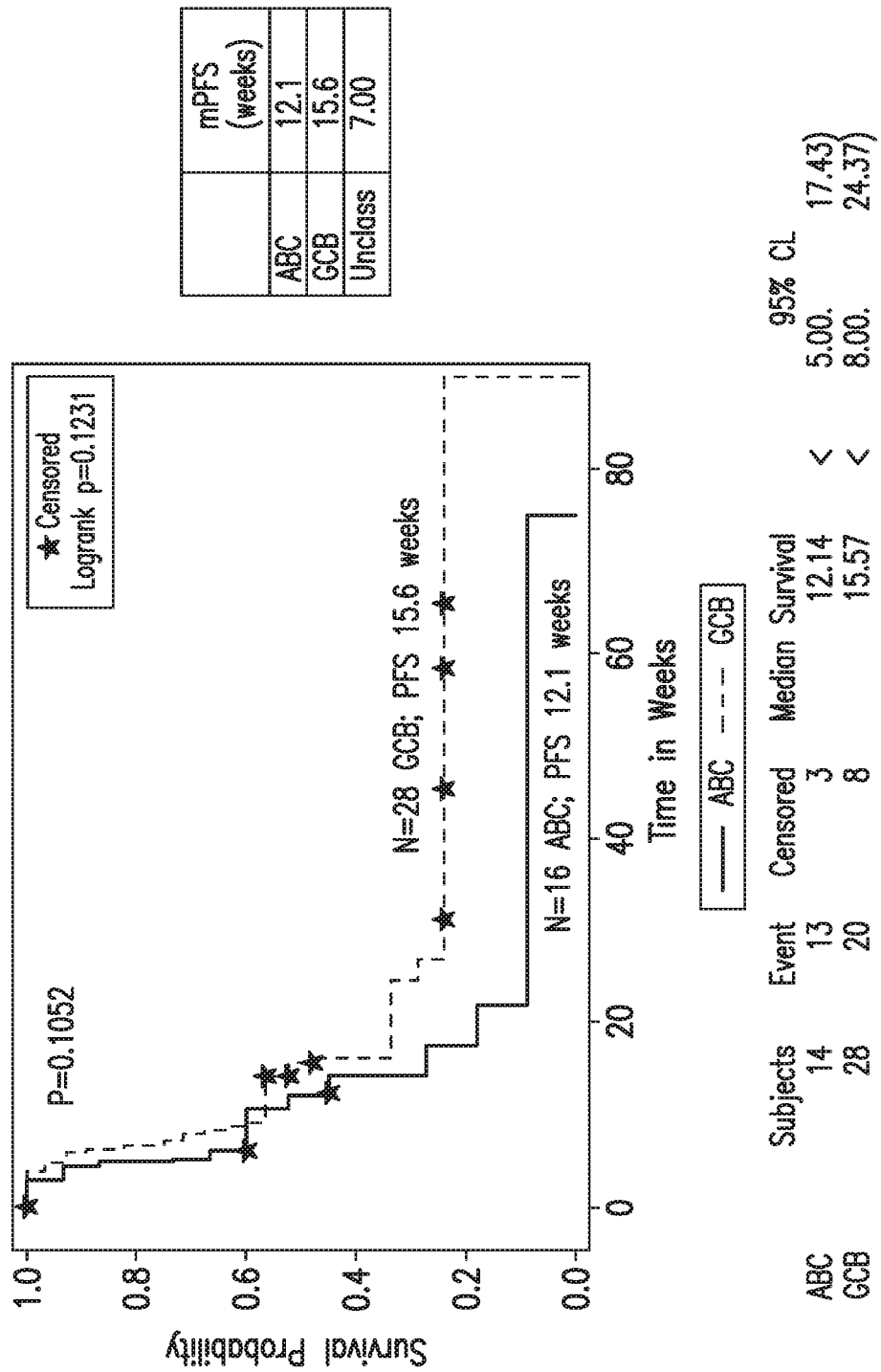
FIG. 7 shows clinical activity of Compound A in the molecular subtypes of DLBCL (Germinal center (GCB), Activated B-cell (ABC), and unclassified) as measured by PFS.

Clinical activity of Compound A in the molecular subtypes of DLBCL (Germinal center (GCB), Activated B-cell (ABC), and unclassified) was analyzed using the Nanostring's lymphocyte specific test (LST), and the results (as shown in FIG. 7) demonstrated no significant difference between the cell of origin subtypes as measured by PFS in response to Compound A treatment (median PFS of 12.1 weeks for ABC versus 15.6 weeks for GCB versus 7 weeks for unclassified, p>0.05 for all combinations).

Figure 8:
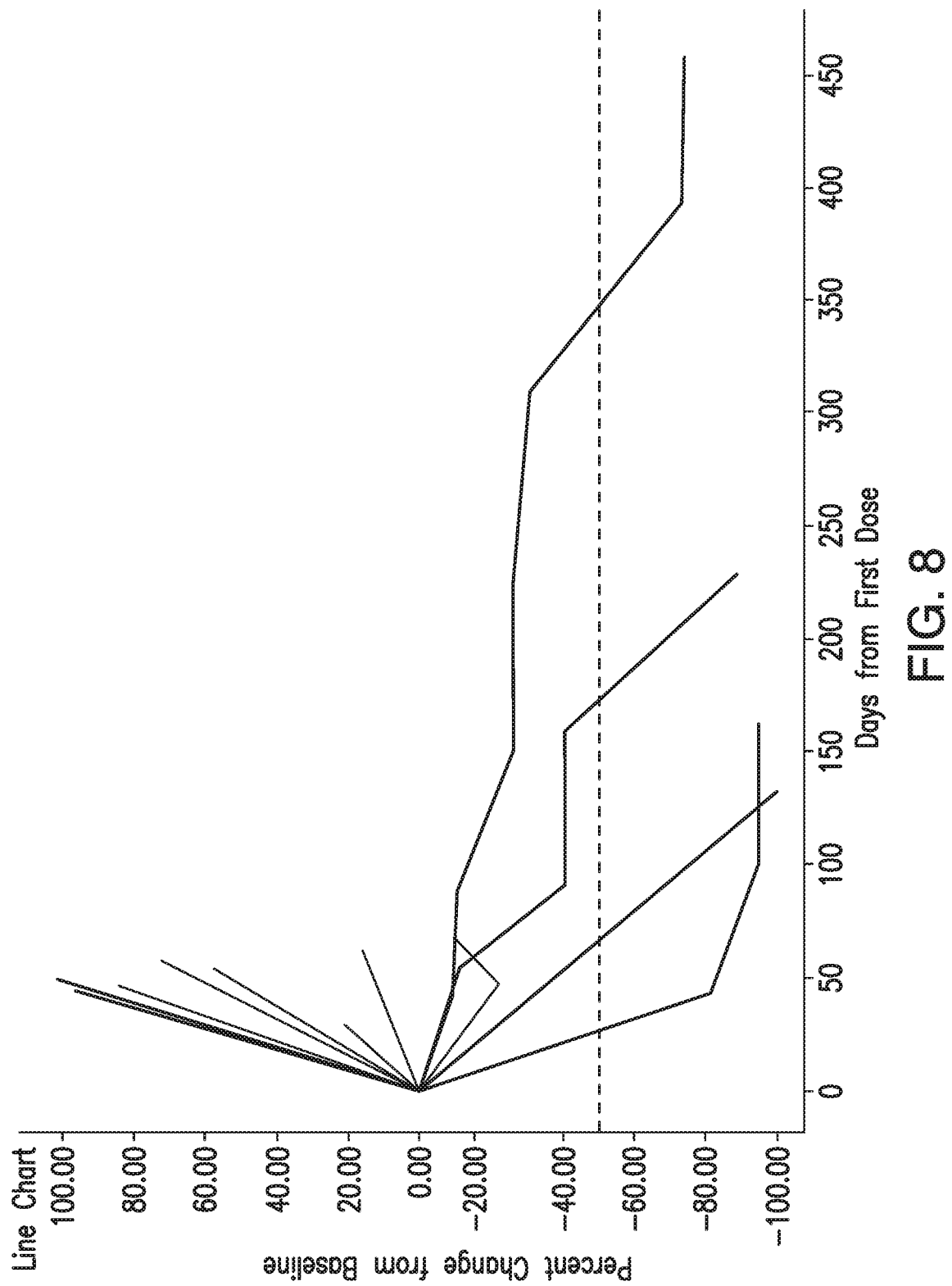
FIG. 8 shows the response to Compound A of DLBCL patients with historically poor prognosis as measured by Nanostring.
Figure 9:
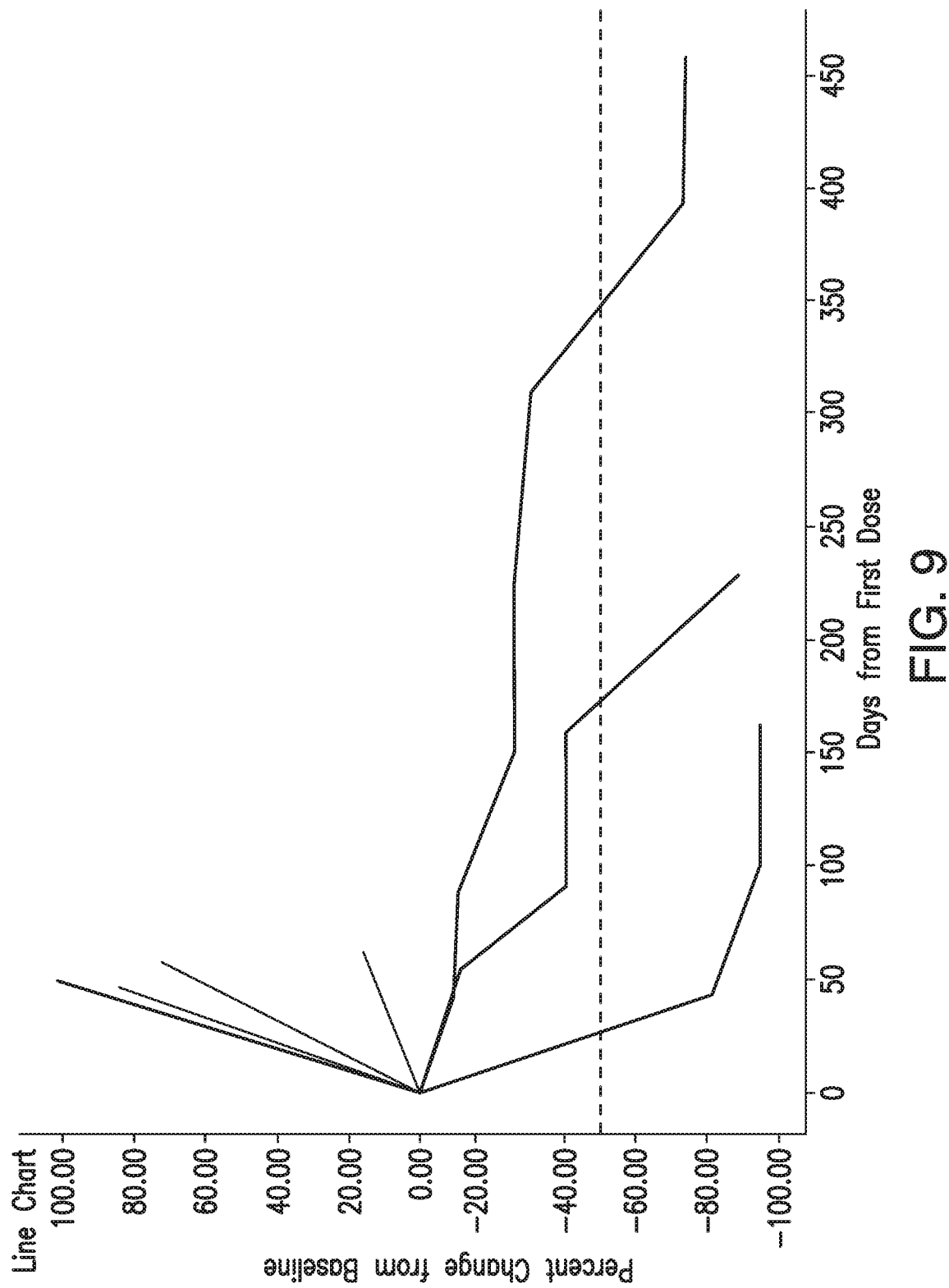
FIG. 9 shows the response to Compound A of primary refractory DLBCL that have had at least 3 or more prior lines of therapies as measured by Nanostring.

Additionally, the response to Compound A of DLBCL patients with historically poor prognosis was measured by Nanostring. Tumors of patients with primary refractory (less than complete response to R-CHOP) disease were measured, and the results show that in response to Compound A treatment, those patients in the 26 genes negative population (pink line) experienced rapid progression. This is comparison to patients in the 26 genes positive population (blue line), in which 4 patients obtained a durable clinical response of greater than 50% decrease in tumor size (see FIG. 8). Similar results were observed when examining patients with primary refractory DLBCL that had also had at least 3 or more prior lines of therapy (see FIG. 9).

These studies demonstrated that the 26 genes of Table 2 can be used to predict the response of a DLBCL patient (e.g., a relapsed or refractory DLBCL patient including both refractory DLBCL patients who have received 1, 2, 3 or more lines of therapies) to Compound A alone or in combination with another agent such as an anti-CD20 antibody (e.g., Rituximab).

5.3 Methods of Treating DLBCL

In one aspect, provided herein are methods for treating a DLBCL patient with lenalidomide or Compound A, wherein the method uses the biomarkers and/or classifiers identified in Table 1, 2 or 3.

In still yet another embodiment, the method for treating a DLBCL patient with a drug comprises: (a) obtaining a first biological sample from a first DLBCL patient; (b) determining the level of expression of one, two, three, four, five or more of the genes identified in Table 1, 2 and/or 3; (c) comparing the level of expression of the one, two, three, four, five or more of the genes identified in Table 1, 2 and/or 3 in the first biological sample with the level of expression of the same genes in a second biological sample(s) from a second DLBCL patient(s), wherein the second DLBCL patient is not responsive to the drug; and (d) administering the drug to the first patient if the one, two, three, four, five or more of the genes in the first biological sample are differentially expressed relative to the level of expression of the one, two, three, four, five or more of the genes in the second biological sample(s), wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof; or a pharmaceutically acceptable salt, solvate, hydrate, co-crystal, clathrate thereof, or a polymorph thereof.

In some embodiments, provided herein are methods for treating a DLBCL patient with a drug comprising: (a) obtaining a first biological sample from a first DLBCL patient; (b) determining the level of expression of one, two, three, four, five or more of the genes identified in Table 1, 2, and/or 3; (c) comparing the level of expression of the one, two, three, four, five or more of the genes identified in Table 1, 2, and/or 3 in the first biological sample with the level of expression of the same genes in a second biological sample(s) from a second DLBCL patient(s), wherein the second DLBCL patient is responsive to the drug; and (d) administering the drug to the first patient if the one, two, three, four, five or more of the genes in the first biological sample are similarly expressed relative to the level of expression of the one, two, three, four, five or more of the genes in the second biological sample(s), wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof; or a pharmaceutically acceptable salt, solvate, hydrate, co-crystal, clathrate thereof, or a polymorph thereof.

In yet another embodiment, the method for treating a DLBCL patient with a drug comprises: (a) obtaining a first biological sample from a first DLBCL patient; (b) determining the expression of the genes or a certain subset of genes set forth in Table 1, 2 and/or 3, or any combination thereof, in the first biological sample, (c) comparing the gene expression profile of the genes or the subset of genes in the first biological sample to (i) the gene expression profile of the genes or the subset of genes in biological samples from DLBCL patients which are responsive to the drug and (ii) the gene expression of the genes or the subset of genes in biological samples from DLBCL patients which are not responsive to the drug; and (d) administering the drug to the first patient if: (i) the gene expression profile for the genes or the subset of genes in the first biological sample is similar to the gene expression profile for the genes or the subset of genes in biological samples from DLBCL patients which are responsive to the drug and (ii) the gene expression profile for the genes or the subset of genes in first biological sample is not similar to the gene expression profile for the genes or the subset of genes in biological samples from DLBCL patients which are not responsive to the drug, wherein the drug is 3-(4-amino-1-oxo-1,3-dihydro-isoindol-2-yl)-piperidine-2, 6-dione (lenalidomide); 3-(5-amino-2-methyl-4-oxo-4H-quinazolin-3-yl)-piperidine-2,6-dione (Compound A); or a stereoisomer thereof; or a pharmaceutically acceptable salt, solvate, hydrate, co-crystal, clathrate thereof; or a polymorph thereof. In some embodiments, the subset(s) of genes are a subset(s) of those genes in Table 1, a subset(s) of those genes in Table 2, and/or a subset(s) of those genes in Table 3, or any combination thereof.

In some embodiments, expression levels of multiple genes (biomarkers) provided herein are used to predict a patient's response to the compound provided herein. When expression levels of multiple genes (biomarkers) are used to predict a patient's response to a treatment with the compound provided herein, e.g., lenalidomide and Compound A, any classifier that classifies based on two or more features can be used in the present disclosure. For example, in some embodiments, a population of DLBCL patients that have received a treatment with the compound provide herein (e.g., lenalidomide or Compound A) are divided into two groups based on their responsiveness to the compound treatment, i.e., responsive patient group and non-responsive patient group. The expression levels of two or more genes provided herein (e.g., those listed in Tables 1-3) for each patient in the population are analyzed using a classifier and a score can be generated. A reference score or a threshold score can be generated based on the scores of the responsive patients and the scores of non-responsive patients. Such reference score can be used to predict a patient's responsiveness to the compound based on the expression levels of the genes of this patient.

In some embodiments, the methods provided herein further comprise (a) generating a score of the sample based on the expression levels of the genes or a subset thereof provided herein in the sample; and (b) determining the probability of the subject being responsive to the compound provided herein by comparing the score of the sample to a reference score.

In some embodiments, the methods provided herein further comprise: (a) determining the expression levels of the genes or a subset thereof provided herein in a biological sample from a population of subjects that previously have been administered with the compound provided herein, (b) generating a score for the expression levels of the genes or a subset thereof provided herein for each subject of the population; (c) differentiating the subjects that are responsive to the compound provided herein from those subjects that are not responsive to the compound provided herein; and (d) determining responsiveness to the compound provided herein based on the scores for the subjects that are responsive to the compound and those subjects that are not responsive to the compound.

In other embodiments, the methods provided herein further comprise: (a) determining the expression levels of the genes or a subset thereof provided herein in a biological sample from a population of subjects that previously have been administered with the compound, (b) generating a score for the expression levels of the genes or a subset thereof provided herein for each subject of the population; (c) differentiating the subjects that are responsive to the compound provided herein from those subjects that are not responsive to compound provided herein; and (d) generating a reference score that is predictive of the responsiveness of a subject to the compound provided herein using a model based on the scores for the subjects that are responsive to the compound and those subjects that are not responsive to the compound.

In another aspect, provided herein are methods for predicting responsiveness of a DLBCL patient to a drug comprising: (a) obtaining a first biological sample from a first DLBCL patient; (b) determining the expression of the genes or a certain subset of genes set forth in Table 1, 2 and/or 3, or any combination thereof, in the first biological sample and generating a score based on the expression of the genes or subset of genes, (c) comparing the score to a reference score, wherein a score similar to a reference score indicates that the patient will be responsive to treatment with the drug. In specific embodiments, the reference score is based on the expression of the same genes or subset of genes in a population of DLBCL patients responsive to the drug. In a specific embodiment, the drug is a compound disclosed herein.

In another aspect, provided herein are methods for treating a DLBCL patient with a drug comprising: (a) obtaining a first biological sample from a first DLBCL patient; (b) determining the expression of the genes or a certain subset of genes set forth in Table 1, 2 and/or 3, or any combination thereof, in the first biological sample and generating a score based on the expression of the genes or subset of genes, (c) comparing the score to a reference score; and (d) administering the drug to the first patient if the score is similar to the reference score. In specific embodiments, the reference score is based on the expression of the same genes or subset of genes in a population of DLBCL patients responsive to the drug. In a specific embodiment, the drug is a compound disclosed herein.

In another aspect, provided herein are methods for treating a DLBCL patient with a drug comprising: (a) obtaining a first biological sample from a first DLBCL patient; (b) determining the expression of the genes or a certain subset of genes set forth in Table 1, 2 and/or 3, or any combination thereof, in the first biological sample and generating a score based on the expression of the genes or subset of genes, (c) comparing the score to a first reference score and a second reference score; and (d) administering the drug to the first patient if the score is similar to the first reference score. In specific embodiments, the first reference score is based on the expression of the same genes or subset of genes in a population of DLBCL patients responsive to the drug and the second reference score is based on the expression of the same genes or subset of genes in a population of DLBCL patients not responsive to the drug. In a specific embodiment, the drug is a compound disclosed herein.

In some embodiments, the determining step of the methods described herein comprising determining the expression of the genes or a certain subset of genes set forth in Table 1 in the first biological sample. For example, in certain embodiments, the subset of genes can include 2, 3, 4, 5, 6, 7, 8, 9, 10, 11, 12, 13, 14, 15, 16, 20, 25 or more genes listed in Table 1. In another embodiment, the subset of genes can include between 2 to 20 genes, or alternatively between 3 to 20 genes, alternatively between 5 to 15 genes, or alternatively 10 to 20 genes listed in Table 1. In some embodiments, the determining step of the methods described herein comprises determining the expression of one or more genes selected from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, and ZNF506.

In some embodiments, the determining step of the methods described herein comprising determining the expression of the genes or a certain subset of genes set forth in Table 2 in the first biological sample. For example, in certain embodiments, the subset of genes can include 2, 3, 4, 5, 6, 7, 8, 9, 10, 11, 12, 13, 14, 15, 16, 20, 25 or more genes listed in Table 2. In another embodiment, the subset of genes can include between 2 to 20 genes, or alternatively between 3 to 20 genes, alternatively between 5 to 15 genes, or alternatively 10 to 20 genes listed in Table 2. In some embodiments, the determining step of the methods described herein comprises determining the expression of one or more genes selected from the group consisting of C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, and ZNF215.

In some embodiments, the determining step of the methods described herein comprising determining the expression of the genes or a certain subset of genes set forth in Table 3 in the first biological sample. For example, in certain embodiments, the subset of genes can include 2, 3, 4, 5, 6, 7, 8, 9, 10, 11, 12, 13, 14, 15, 16, 19 or more genes listed in Table 3. In another embodiment, the subset of genes can include between 2 to 19 genes, or alternatively between 3 to 19 genes, alternatively between 5 to 15 genes, or alternatively 10 to 19 genes listed in Table 3. In some embodiments, the determining step of the methods described herein comprises determining the expression of one or more genes selected from the group consisting of BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1. In some embodiments, the subset of genes includes BMS1P20, MZB1, TNFRSF17, FKBP11, and IGLV1-44. In other embodiments, the subset of genes includes MS4A1, BCL11A, MACROD2, and FAM129C. In yet other embodiments, the subset of genes includes ALDH2, KIAA1598, TGFBI, TYMP, and SAMD4A. In yet other embodiments, the subset of genes includes GPX3, A2M, CFB, FSTL1, SLC27A3, and NRP1.

In some embodiments, the determining step of the methods described herein comprising determining the expression of the genes or a certain subset of genes set forth in a combination of Tables 1, 2, and 3 in the first biological sample. For example, in certain embodiments, the subset of genes can include 2, 3, 4, 5, 6, 7, 8, 9, 10, 11, 12, 13, 14, 15, 16, 20, 25, 30, 35, 40, 50, 60, 70 or more genes listed in Tables 1, 2, and 3. In another embodiment, the subset of genes can include between 2 to 71 genes, or alternatively between 2 to 20 genes, or alternatively between 3 to 20 genes, alternatively between 5 to 15 genes, or alternatively 10 to 20 genes listed in Tables 1, 2, and 3. In some embodiments, In some embodiments, the determining step of the methods described herein comprises determining the expression of one or more genes (biomarkers) selected from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, ZNF506, C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, ZNF215, BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1.

In one embodiment, the biomarker is ANXA4. In another embodiment, the biomarker is BACH2. In another embodiment, the biomarker is BIN2. In another embodiment, the biomarker is C7orf10. In another embodiment, the biomarker is CXCL14. In yet another embodiment, the biomarker is DAPL1. In yet another embodiment, the biomarker is FBXO32. In yet another embodiment, the biomarker is FCGR1B. In yet another embodiment, the biomarker is FTX. In yet another embodiment, the biomarker is GIMAP6. In yet another embodiment, the biomarker is IL18BP. In yet another embodiment, the biomarker is KCNMB1. In yet another embodiment, the biomarker is KIAA1671. In yet another embodiment, the biomarker is LOC284837. In yet another embodiment, the biomarker is MPP6. In yet another embodiment, the biomarker is MZT1. In yet another embodiment, the biomarker is NFIC. In yet another embodiment, the biomarker is ODF3B. In yet another embodiment, the biomarker is OLFM1. In yet another embodiment, the biomarker is PPAT. In yet another embodiment, the biomarker is RFESD. In yet another embodiment, the biomarker is RPL22L1. In yet another embodiment, the biomarker is SERPING1. In yet another embodiment, the biomarker is TNC. In yet another embodiment, the biomarker is TNFRSF17. In yet another embodiment, the biomarker is ZNF506. In yet another embodiment, the biomarker is C10orf54. In yet another embodiment, the biomarker is C1RL. In yet another embodiment, the biomarker is C20orf112. In yet another embodiment, the biomarker is C8orf4. In yet another embodiment, the biomarker is CCDC88C. In yet another embodiment, the biomarker is CILP. In yet another embodiment, the biomarker is CIRH1A. In yet another embodiment, the biomarker is CLU. In yet another embodiment, the biomarker is CPVL. In yet another embodiment, the biomarker is CSF1R. In yet another embodiment, the biomarker is CTSB. In yet another embodiment, the biomarker is EPB41L3. In yet another embodiment, the biomarker is FBXO32. In yet another embodiment, the biomarker is IFI44. In yet another embodiment, the biomarker is LRP11. In yet another embodiment, the biomarker is MEGF6. In yet another embodiment, the biomarker is MEIS1. In yet another embodiment, the biomarker is PHACTR2. In yet another embodiment, the biomarker is PLAT. In yet another embodiment, the biomarker is SERPING1. In yet another embodiment, the biomarker is SPC25. In yet another embodiment, the biomarker is THEMIS2. In yet another embodiment, the biomarker is TPSAB1. In yet another embodiment, the biomarker is ULK1. In yet another embodiment, the biomarker is XAF1. In yet another embodiment, the biomarker is ZNF215. In yet another embodiment, the biomarker is BMS1P20. In yet another embodiment, the biomarker is MZB1. In yet another embodiment, the biomarker is TNFRSF17. In yet another embodiment, the biomarker is FKBP11. In yet another embodiment, the biomarker is IGLV1-44. In yet another embodiment, the biomarker is MS4A1. In yet another embodiment, the biomarker is BCL11A. In yet another embodiment, the biomarker is MACROD2. In yet another embodiment, the biomarker is FAM129C. In yet another embodiment, the biomarker is ALDH2. In yet another embodiment, the biomarker is KIAA1598. In yet another embodiment, the biomarker is TGFBI. In yet another embodiment, the biomarker is TYMP. In yet another embodiment, the biomarker is SAMD4A. In yet another embodiment, the biomarker is GPX3. In yet another embodiment, the biomarker is A2M. In yet another embodiment, the biomarker is CFB. In yet another embodiment, the biomarker is FSTL1. In yet another embodiment, the biomarker is SLC27A3. In yet another embodiment, the biomarker is NRP1.

In certain embodiments, in accordance with the methods described herein, the gene expression provide or data is derived from the same type of biological sample. In other words, the biological sample used to generate each gene expression profile or data referenced in the methods is the same type of biological sample. In some embodiments, the biological samples are tumor biopsy samples.

In some embodiments, the determining step of the methods described herein comprise detecting the presence and/or amount of a complex in the biological sample, wherein the presence and/or amount of the complex indicates the expression level of the genes. The complex detected in the methods described herein can be a hybridization complex and in some embodiments, the hybridization complex is attached to a solid support. In further embodiments, the complex is detectably labeled.

In some embodiments, the determining step of the methods described herein comprise detecting the presence and/or amount of a reaction product in the biological sample, wherein the presence and/or amount of the reaction product indicates the expression level of the genes in each subset of genes. In further embodiments, the reaction product is detectably labeled.

In some embodiments, the expression of the genes or biomarkers provided herein is determined by determining the protein levels of the genes or biomarkers. In other embodiments, the expression of the genes or biomarkers provided herein is determined by determining the mRNA levels of the genes or biomarkers. In yet other embodiments, the expression of the genes provided herein is determined by determining the levels of cDNA generated using mRNA of the genes or biomarkers. Accordingly, the upregulation or downregulation of nucleic acids (e.g., mRNA or cDNA) or proteins of the genes provided herein (e.g., those listed in Tables 1-3) can be used to predict a DLBCL patient's response to a compound treatment.

In some embodiments, a statistical analysis or other analysis is performed on data from the assay utilized to measure an RNA transcript or protein. In certain specific embodiments, the p value of those RNA transcripts or proteins differentially expressed is 0.1, 0.5, 0.4, 0.3, 0.2, 0.01, 0.05, 0.001, or 0.0001. In some embodiments, the p-value provided herein is the output of a statistical test of difference between two or more groups of values or data examples. In specific embodiments, a false discovery rate (FDR) of 10%, 9%, 8%, 7%, 6%, 5%, 4%, 3%, 2% or less is selected. FDR correction and associated thresholds are commonly applied to correct p-values for multiple hypothesis testing, i.e. applying the same test or comparison to many groups of values before seeking to assign statistical significance to a subset of the differences observed. In some embodiments, hypothesis testing for difference may also be applied to output of a functional transformation of assay output. In some embodiments, additional processes other than tests of difference can be used to classify or predict drug response from assay output.

In some embodiments, the methods described herein include predicting responsiveness of a DLBCL patient, wherein the DLBCL is refractory in the DLBCL patient.

In some embodiments, the methods described herein include predicting responsiveness of a DLBCL patient, wherein the DLBCL is relapsed in the DLBCL patient.

In some embodiments, the methods described herein include predicting responsiveness of a DLBCL patient, wherein the DLBCL is a germinal center B-cell-like subtype in the DLBCL patient.

In some embodiments, the methods described herein include predicting responsiveness of a DLBCL patient, wherein the DLBCL is activated B-cell like in the DLBCL patient.

In some embodiments, the methods described herein include predicting responsiveness of a DLBCL patient, wherein the DLBCL is Type III in the DLBCL patient.

In some embodiments, the methods described herein include determining the gene expression profile of a subset(s) of genes in DLBCL patients that have taken the drug prior to treatment with the drug, wherein each subset of genes relates to a tumor biopsy composition.

In certain embodiments, the drug is administered to a DLBCL patient as a dose of from about 0.1 mg per day to about 100 mg per day. In other embodiments, the drug is administered a DLBCL patient as a dose of between about 0.5 mg per day to about 100 mg per day. In other embodiments, the drug is administered a DLBCL patient as a dose of between about 0.5 mg per day to about 20 mg per day. In other embodiments, the drug is administered a DLBCL patient as a dose of between about 5 mg per day to about 25 mg per day. In some embodiments, the drug is administered a DLBCL patient as a dose of between about 0.5 mg per day to about 10 mg per day. In certain embodiments, the drug is administered a DLBCL patient as a dose of between about 0.5 mg per day to about 100 mg per day.

In other embodiments, the drug is administered at a dose of about 0.1 mg, 0.5 mg, 1 mg, 1.5 mg, 2 mg, 2.5 mg, 3 mg, 3.5 mg, 4.0 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 20 mg, 25 mg, 30 mg, 35 mg, 40 mg, 45 mg, 50 mg, 60 mg, 70 mg, 80 mg, 90 mg or 100 mg per day.

In some embodiments, the drug is administered once daily. In some embodiments, the drug is administered twice daily. In certain embodiments, the drug is cyclically administered to a patient with DLBCL. Cycling therapy involves the administration of an active agent for a period of time, followed by a rest for a period of time, and repeating this sequential administration. Accordingly, in some embodiments, about 0.5 mg per day to about 100 mg per day of the drug is administered on days 1-12 of a repeated 28 day cycle. In a specific embodiment, 25 mg of the drug is administered once a day on days 1-12 of a repeated 28 day cycle. In some embodiments, the drug is administered on an intermittent dosing schedule. In a specific embodiment, 2 mg or 3 mg of the drug (e.g., lenalidomide or Compound A) is administered daily for 5 continuous days out of 7 days a week.

It is understood that specific dose levels of a drug described for any particular subject depends upon a variety of factors including the activity of the specific compound employed, the age, body weight, general health, sex, and diet of the patient, the time of administration, the rate of excretion, the drug combination, and the severity of the DLBCL being treated and form of administration. In it also understand that one of ordinary skill in the art can readily determine the appropriate dose of the drug based on these factors. Treatment dosages generally may be titrated to optimize safety and efficacy.

A drug can be administered by any route of administration known in the art such as oral, intravenous, subcutaneous, or intramucosal administration. In one embodiment, lenalidomide or a stereoisomer thereof; or a pharmaceutically acceptable salt, solvate, hydrate, co-crystal, clathrate thereof; or a polymorph thereof, is administered to a DLBCL patient orally. In one embodiment, Compound A or a stereoisomer thereof, or a pharmaceutically acceptable salt, solvate, hydrate, co-crystal, clathrate thereof; or a polymorph thereof, is administered to a DLBCL patient orally. In some embodiments, a combination of lenalidomide or a stereoisomer thereof; or a pharmaceutically acceptable salt, solvate, hydrate, co-crystal, clathrate thereof; or a polymorph thereof, and Compound A, a stereoisomer thereof; or a pharmaceutically acceptable salt, solvate, hydrate, co-crystal, clathrate thereof; or a polymorph thereof is administered to the DLBCL patient orally. The oral dosage form can be a tablet or a capsule. In some embodiments, the dosage form is a tablet. In some other embodiments, the dosage for is a capsule.

In one embodiment, the drug described herein can be combined with another therapy, such as described in Section 5.5, infra.

5.4 Treatment Compounds

5.4.1 3-(4-amino-1-oxo-1,3-dihydro-isoindol-2-yl)-piperidine-2,6-dione (lenalidomide)

In some embodiments, the compound administered to a DLBCL patient is 3-(4-amino-1-oxo-1,3-dihydro-isoindol-2-yl)-piperidine-2,6-dione (lenalidomide; REVLIMID®), or a stereoisomer thereof, or a pharmaceutically acceptable salt, solvate, hydrate, co-crystal, clathrate thereof; or a polymorph thereof. Such compounds can be formulated for the appropriate route of administration using techniques known in the art.

5.4.2 Preparation of 3-(4-amino-1-oxo-1,3-dihydro-isoindol-2-yl)-piperidine-2,6-dione (lenalidomide)

Methyl 2-bromomethyl-3-nitrobenzoate

A stirred mixture of methyl 2-methyl-3-nitrobenzoate (14.0 g, 71.7 mmol) and N-bromosuccinimide (15.3 g, 86.1 mmol) in carbon tetrachloride (200 mL) was heated under gentle reflux for 15 hours while a 100 W bulb situated 2 cm away was shining on the flask. The mixture was filtered and the solid was washed with methylene chloride (50 mL). The filtrate was washed with water (2×100 mL), brine (100 mL) and dried. The solvent was removed in vacuo and the residue was purified by flash chromatography (hexane/ethyl acetate, 8/2) to afford 19 g (96%) of the product as a yellow solid: mp 70.0-71.5° C.; 1H NMR (CDCl$_3$) $\delta$ 8.12-8.09 (dd, J=1.3 and 7.8 Hz, 1H), 7.97-7.94 (dd, J=1.3 and 8.2 Hz, 1H), 7.54 (t, J=8.0 Hz, 1H). 5.15 (s, 2H), 4.00 (s, 3H); $^{13}$C NMR (CDCl$_3$) $\delta$ 165.85, 150.58, 134.68, 132.38, 129.08, 127.80, 53.06, 22.69; HPLC, Water Nove-Pak/C18, 3.9×150 mm, 4 micron, 1 mL/min, 240 nm, 40/60 CH$_3$CN/0.1% H$_3$PO$_4$ (aq) 7.27 min(98.92%); Anal. Calcd for C$_9$H$_8$NO$_4$Br: C, 39.44; H, 2.94; N, 5.11; Br, 29.15. Found: C, 39.46; H, 3.00; N, 5.00; Br, 29.11.

t-Butyl N-(1-oxo-4-nitroisoindolin-2-yl)-L-glutamine

Triethylamine (2.9 g, 28.6 mmol) was added dropwise to a stirred mixture of methyl 2-bromomethyl-3-nitrobenzoate (3.5 g, 13.0 mmol) and L-glutamine t-butyl ester hydrochloride (3.1 g, 13.0 mmol) in tetrahydrofuran (90 mL). The mixture was heated to reflux for 24 hours. To the cooled mixture was added methylene chloride (150 mL) and the mixture was washed with water (2×40 mL), brine (40 mL) and dried. The solvent was removed in vacuo and the residue was purified by flash chromatography (3% $CH_3OH$ in methylene chloride) to afford 2.84 g (60%) of crude product which was used directly in the next reaction: 1H NMR ($CDCl_3$) δ 8.40 (d, J=8.1 Hz, 1H), 8.15 (d, J=7.5 Hz, 1H), 7.71 (t, J=7.8 Hz, 1H), 5.83 (s, 1H), 5.61 (s, 1H), 5.12 (d, J=19.4 Hz, 1H), 5.04-4.98 (m, 1H), 4.92 (d, J=19.4 Hz, 1H), 2.49-2.22 (m, 4H). 1.46 (s, 9H); HPLC, Waters Nova-Pak C18, 3.9×150 mm, 4 micron, 1 mL/min, 240 nm, 25/75 $CH_3CN$/0.1% $H_3PO_4$ (aq) 6.75 min(99.94%).

N-(1-oxo-4-nitroisoindolin-2-yl)-L-glutamine

Hydrogen chloride gas was bubbled into a stirred 5° C. solution of t-butyl N-(1-oxo-4-nitro-isoindolin-2-yl)-L-glutamine (3.6 g, 9.9 mmol) in methylene chloride (60 mL) for 1 hour. The mixture was then stirred at room temperature for another hour. Ether (40 mL) was added and the resulting mixture was stirred for 30 minutes. The slurry was filtered, washed with ether and dried to afford 3.3 g of the product: 1H NMR (DMSO-$d_6$) δ 8.45 (d, J=8.1 Hz, 1H), 8.15 (d, J=7.5 Hz, 1H), 7.83 (t, J=7.9 Hz. 1H), 7.24 (s, 1H), 6.76 (s, 1H), 4.93 (s, 2H), 4.84-4.78 (dd, J=4.8 amd 10.4 Hz, 1H), 2.34-2.10 (m, 4H); $^{13}C$ NMR (DMSO-$d_6$) δ 173.03, 171.88, 165.96, 143.35, 137.49, 134.77, 130.10, 129.61, 126.95, 53.65, 48.13, 31.50, 24.69; Anal. Calcd for $C_{13}H_{13}N_3O_6$: C, 50.82; H, 4.26; N, 13.68. Found: C, 50.53; H. 4.37; N, 13.22.

(S)-3-(1-oxo-4-nitroisoindolin-2-yl)piperidine-2,6-dione

A stirred suspension mixture of N-(1-oxo-4-nitroisoindolin-2-yl)-L-glutamine (3.2 g, 10.5 mmol) in anhydrous methylene chloride (150 mL) was cooled to −40° C. with isopropanol/dry ice bath. Thionyl chloride (0.82 mL, 11.3 mmol) was added dropwise to the cooled mixture followed by pyridine (0.9 g. 11.3 mmol). After 30 min, triethylamine (1.2 g, 11.5 mmol) was added and the mixture was stirred at −30 to −40° C. for 3 hours. The mixture was poured into ice water (200 mL) and the aqueous layer was extracted with methylene chloride (40 mL). The methylene chloride solution was washed with water (2×60 mL), brine (60 mL) and dried. The solvent was removed in vacuo and the solid residue was slurried with ethyl acetate (20 mL) to give 2.2 g (75%) of the product as a white solid: mp 285° C.; 1H NMR (DMSO-$d_6$) δ1.04 (s, 1H), 8.49-8.45 (dd, J=0.8 and 8.2 Hz, 1H), 8.21-8.17 (dd, J=7.3 Hz, 1H), 7.84 (t, J=7.6 Hz, 1H), 5.23-5.15 (dd, J=4.9 and 13.0 Hz, 1H), 4.96 (dd, J=19.3 and 32.4 Hz, 2H), 3.00-2.85 (m, 1H), 2.64-2.49 (m, 2H), 2.08-1.98 (m, 1H); $^{13}C$ NMR (DMSO-$d_6$) δ 172.79, 170.69, 165.93, 143.33, 137.40, 134.68, 130.15, 129.60, 127.02, 51.82, 48.43, 31.16, 22.23; HPLC, Waters Nove-Pak/C18, 3.9×150 mm, 4 micron, 1 mL/min, 240 nm, 20/80 $CH_3CN$/ 0.1% $H_3PO_4$ (aq) 3.67 min(100%); Anal. Calcd for $C_{13}H_nN_3O_5$: C, 53.98; H, 3.83; N, 14.53. Found: C, 53.92; H, 3.70; N, 14.10.

3-(4-amino-1-oxo-1,3-dihydro-isoindol-2-yl)-piperidine-2,6-dione

A mixture of (S)-3-(1-oxo-4-nitroisoindolin-2-yl)piperidine-2,6-dione (1.0 g, 3.5 mmol) and 10% Pd/C (0.3 g) in methanol (600 mL) was hydrogenated in a Parr-Shaker apparatus at 50 psi of hydrogen for 5 hours. The mixture was filtered through Celite and the filtrate was concentrated in vacuo. The solid was slurried in hot ethyl acetate for 30 min, filtered and dried to afford 0.46 g (51%) of the product as a white solid: mp 235.5-239° C.; $^1H$ NMR (DMSO-$d_6$) δ 11.01 (s, 1H). 7.19 (t, J=7.6 Hz, 1H). 6.90 (d. J=7.3 Hz, 1H), 6.78 (d, J=7.8 Hz, 1H), 5.42 (s, 2H). 5.12 (dd. J=5.1 and 13.1 Hz, 1H), 4.17 (dd, J=17.0 and 28.8 Hz, 2H), 2.92-2.85 (m, 1H). 2.64-2.49 (m, 1H). 2.34-2.27 (m, 1H), 2.06-1.99 (m, 1H); $^{13}C$ NMR (DMSO-$d_6$) δ 172.85, 171.19, 168.84, 143.58, 132.22, 128.79, 125.56, 116.37, 110.39, 51.48, 45.49, 31.20, 22.74; HPLC. Waters Nova-Pak/C18, 3.9×150 mm, 4 micron, 1 mL/min, 240 nm, 10/90 $CH_3CN$/0.1% $H_3PO_4$ (aq) 0.96 min(100%); Chiral analysis, Daicel Chiral Pak AD, 40/60 Hexane/IPA, 6.60 min(99.42%); Anal. Calcd for $C_{13}H_{13}N_3O_3$: C, 60.23; H, 5.05; N, 16.21. Found: C, 59.96; H. 4.98; N, 15.84.

3-(4-Amino-1-oxo-1,3-dihydro-isoindol-2-yl)-piperidine-2,6-dione may also be prepared by methods known in the art, for example, as provided in *Drugs of the Future*, 2003, 28(5): 425-431, the entirety of which is incorporated by reference.

5.4.3 3-(5-amino-2-methyl-4-oxo-4H-quinazolin-3-yl)-piperidine-2,6-dione (Compound A)

In some embodiments, the compound administer to a patient is 3-(5-amino-2-methyl-4-oxo-4H-quinazolin-3-yl)-piperidine-2,6-dione ("Compound A"), which has the following structure:

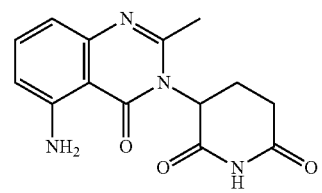

A or a stereoisomer thereof, or a pharmaceutically acceptable salt, solvate, hydrate, co-crystal, clathrate thereof; or a polymorph thereof. Such compounds can be formulated for the appropriate route of administration using techniques known in the art.

Compound A can be prepared as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Pat. No. 8,802,685, issued Aug. 12, 2014, which is incorporated herein by reference in its entirety. In some embodiments, the hydrochloride salt of Compound A is used in the methods provided herein. Methods of treating, preventing and/or managing cancers and other diseases using Compound A are described in U.S. Publication No. 2012/0230983, published Sep. 12, 2012, which is incorporated herein by reference in its entirety.

5.4.4 Preparation of Compound A

To a solution of potassium hydroxide (16.1 g, 286 mmol) in water (500 mL), was added 3-nitrophthalimide (25.0 g, 130 mmol) in portion at 0° C. The suspension was stirred at 0° C. for 3 hrs, and then heated to 30° C. for 3 hrs. To the solution, was added HCl (100 mL, 6N). The resulting suspension was cooled to 0° C. for 1 hr. The suspension was filtered and washed with cold water (2×10 mL) to give 3-nitro-phthalamic acid as a white solid (24.6 g, 90% yield): $^1$H NMR (DMSO-d$_6$) δ 7.69 (brs, 1H, NHH), 7.74 (t, J=8 Hz, 1H, Ar), 7.92 (dd, J=1, 8 Hz, 1H, Ar), 8.13 (dd, J=1, 8 Hz, 1H, Ar), 8.15 (brs, 1H, NHH), 13.59 (s, 1H, OH); $^{13}$C NMR (DMSO-d$_6$) δ 125.33, 129.15, 130.25, 132.54, 136.72, 147.03, 165.90, 167.31.

To a mixture of 3-nitro-phthalamic acid (24.6 g, 117 mmol) and potassium hydroxide (6.56 g, 117 mmol) in water (118 mL), was added a mixture of bromine (6 mL), potassium hydroxide (13.2 g, 234 mmol) in water (240 mL) at 0° C., followed by addition of a solution of potassium hydroxide (19.8 g, 351 mmol) in water (350 mL). After 5 minutes at 0° C., the mixture was heated in a 100° C. oil bath for 1 hr. The reaction solution was cooled to room temperature, and then, in an ice-water bath for 30 minutes. To the mixture, a solution of HCl (240 mL, 2N) was added dropwise at 0° C., and the resulting mixture was kept for 1 hr. The suspension was filtered and washed with water (5 mL) to give 2-amino-6-nitro-benzoic acid as yellow solid (15.6 g, 73% yield): HPLC: Waters Symmetry C$_{18}$, 5 μm, 3.9×150 mm, 1 mL/min, 240 nm, CH$_3$CN/0.1% H$_3$PO$_4$, 5% grad to 95% over 5 min, 5.83 min (85%); $^1$H NMR (DMSO-d$_6$) δ 6.90 (dd, J=1, 8 Hz, 1H, Ar), 7.01 (dd, J=1, 9 Hz, 1H, Ar), 7.31 (t, J=8 Hz, 1H, Ar), 8.5-9.5 (brs, 3H, OH, NH$_2$); $^{13}$C NMR (DMSO-d$_6$) δ 105.58, 110.14, 120.07, 131.74, 149.80, 151.36, 166.30; LCMS: MH=183.

A mixture of 2-amino-6-nitro-benzoic acid (1.5 g, 8.2 mmol) in acetic anhydride (15 mL) was heated at 200° C. for 30 minutes in a microwave oven. The mixture was filtered and washed with ethyl acetate (20 mL). The filtrate was concentrated in vacuo. The solid was stirred in ether (20 mL) for 2 hrs. The suspension was filtered and washed with ether (20 mL) to give 2-methyl-5-nitro-benzo[d][1,3]oxazin-4-one as a light brown solid (1.4 g, 85% yield): HPLC: Waters Symmetry C$_{18}$, 5 μm, 3.9×150 mm, 1 mL/min, 240 nm, CH$_3$CN/0.1% H$_3$PO$_4$, 5% grad 95% in 5 min, 5.36 min (92%); $^1$H NMR (DMSO-d$_6$) δ 2.42 (s, 3H, CH$_3$), 7.79 (dd, J=1, 8 Hz, 1H, Ar), 7.93 (dd, J=1, 8 Hz, 1H, Ar), 8.06 (t, J=8 Hz, 1H, Ar); $^{13}$C NMR (DMSO-d$_6$) δ 20.87, 107.79, 121.54, 128.87, 137.19, 147.12, 148.46, 155.18, 161.78; LCMS: MH=207.

Two vials each with a suspension of 5-nitro-2-methyl-benzo[d][1,3]oxazin-4-one (0.60 g, 2.91 mmol) and 3-amino-piperidine-2,6-dione hydrogen chloride (0.48 g, 2.91 mmol) in pyridine (15 mL) were heated at 170° C. for 10 minutes in a microwave oven. The suspension was filtered and washed with pyridine (5 mL). The filtrate was concentrated in vacuo. The resulting mixture was stirred in HCl (30 mL, 1N), ethyl acetate (15 mL) and ether (15 mL) for 2 hrs. The suspension was filtered and washed with water (30 mL) and ethyl acetate (30 mL) to give a dark brown solid, which was stirred with methanol (50 mL) at room temperature overnight. The suspension was filtered and washed with methanol to give 3-(2-methyl-5-nitro-4-oxo-4H-quinazolin-3-yl)-piperidine-2,6-dione as a black solid (490 mg, 27% yield). The solid was used in the next step without further purification.

A mixture of 3-(2-methyl-5-nitro-4-oxo-4H-quinazolin-3-yl)-piperidine-2,6-dione (250 mg) and Pd(OH)$_2$ on carbon (110 mg) in DMF (40 mL) was shaken under hydrogen (50 psi) for 12 hrs. The suspension was filtered through a pad of Celite and washed with DMF (10 mL). The filtrate was concentrated in vacuo and the resulting oil was purified by flash column chromatography (silica gel, methanol/methylene chloride) to give 3-(5-amino-2-methyl-4-oxo-4H-quinazolin-3-yl)-piperidine-2,6-dione as a white solid (156 mg, 69% yield): HPLC: Waters Symmetry C$_{18}$, 5 μm, 3.9×150 mm, 1 mL/min, 240 nm, 10/90 CH$_3$CN/0.1% H$_3$PO$_4$, 3.52 min (99.9%); mp: 293-295° C.; $^1$H NMR (DMSO-d$_6$) δ 2.10-2.17 (m, 1H, CHH), 2.53 (s, 3H, CH$_3$), 2.59-2.69 (m, 2H, CH$_2$), 2.76-2.89 (m, 1H, CHH), 5.14 (dd, J=6, 11 Hz, 1H, NCH), 6.56 (d, J=8 Hz, 1H, Ar), 6.59 (d, J=8 Hz, 1H, Ar), 7.02 (s, 2H, NH$_2$), 7.36 (t, J=8 Hz, 1H, Ar), 10.98 (s, 1H, NH); $^{13}$C NMR (DMSO-d$_6$) δ 20.98, 23.14, 30.52, 55.92, 104.15, 110.48, 111.37, 134.92, 148.17, 150.55, 153.62, 162.59, 169.65, 172.57; LCMS: MH=287; Anal. Calcd. for C$_{14}$H$_{14}$N$_4$O$_3$+0.3H$_2$O: C, 57.65; H, 5.05; N, 19.21. Found: C, 57.50; H, 4.73; N, 19.00.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.5 Combination Therapy

One or more additional therapies, such as additional active ingredients or agents, that can be used in combination with the administration of a drug described herein to treat a DLBCL patient. In a specific embodiment, one or more additional active ingredients or agents can be used in the methods provided herein with a drug. The one or more additional therapies can be administered prior to, concurrently with, or subsequent to the administration of a drug described herein. Administration of a drug described herein and an additional active agent to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated. Routes of administration for the additional active agents or ingredients are known to those of ordinary skill in the art. See, e.g., *Physicians' Desk Reference*.

In certain embodiments, a drug described herein and an additional active agent are cyclically administered to a patient with a hematological cancer (e.g., DLBCL). Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

The additional active agents administered in combination with a drug described herein can be large molecules (e.g., proteins) or small molecules (e.g., synthetic inorganic, organometallic, or organic molecules). In certain embodiments, the additional active agent is an immunomodulatory therapy. In other embodiments, the additional active agent is not a drug described herein. Examples of large molecule active agents include, but are not limited to, hematopoietic growth factors, cytokines, and monoclonal and polyclonal antibodies. In certain embodiments, large molecule active agents are biological molecules, such as naturally occurring or artificially made proteins. Proteins that are useful include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the disclosure include, but are not limited to: filgrastim, which is sold in the United States under the trade name NEUPOGEN® (Amgen, Thousand Oaks, Calif.); sargramostim, which is sold in the United States under the trade name LEUKINE® (Immunex, Seattle, Wash.); and recombinant EPO, which is sold in the United States under the trade name EPGEN® (Amgen, Thousand Oaks, Calif.).

Inhibitors of ActRII receptors or activin-ActRII inhibitors may be used in the methods and compositions provided herein. ActRII receptors include ActRIIA inhibitors and ActRIIB inhibitors. Inhibitors of ActRII receptors can be polypeptides comprising activin-binding domains of ActRII. In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). In certain embodiments, the activin-binding domain is linked to an Fc portion of an antibody via a linker, e.g., a peptide linker. Examples of such non-antibody proteins selected for activin or ActRIIA binding and methods for design and selection of the same are found in WO/2002/088171, WO/2006/055689, WO/2002/032925, WO/2005/037989, US 2003/0133939, and US 2005/0238646, each of which is incorporated herein by reference in its entirety.

Recombinant and mutated forms of GM-CSF can be prepared as described in U.S. Pat. Nos. 5,391,485; 5,393,870; and 5,229,496; the disclosure of each of which is incorporated herein by reference in its entirety. Recombinant and mutated forms of G-CSF can be prepared as described in U.S. Pat. Nos. 4,810,643; 4,999,291; 5,528,823; and 5,580,755; the disclosure of each of which is incorporated herein by reference in its entirety.

This disclosure encompasses the use of native, naturally occurring, and recombinant proteins. The disclosure further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001).

Antibodies that can be used in combination with a drug described herein include monoclonal and polyclonal antibodies. Examples of antibodies include, but are not limited to, trastuzumab (HERCEPTIN), rituximab (RITUXAN®), bevacizumab (AVASTIN®), pertuzumab (OMNITARG™), tositumomab (BEXXAR®), edrecolomab (PANOREX®), panitumumab and G250. An immunomodulatory therapy provided herein can also be combined with or used in combination with anti-TNF-alpha antibodies.

Large molecule active agents may be administered in the form of anti-cancer vaccines. For example, vaccines that secrete, or cause the secretion of, cytokines such as IL-2, SCF, CXC14 (platelet factor 4), G-CSF, and GM-CSF can be used in the methods, pharmaceutical compositions, and kits of the disclosure. See, e.g., Emens, L. A., et al., Curr. Opinion Mol. Ther. 3(1):77-84 (2001).

Additional active agents that are small molecules can also be used to alleviate adverse effects associated with the administration of a drug described herein. However, like some large molecules, many are believed to be capable of providing a synergistic effect when administered with (e.g., before, after or simultaneously) the immunomodulatory therapy. Examples of small molecule additional active agents include, but are not limited to, anti-cancer agents, antibiotics, immunosuppressive agents, and steroids.

Examples of anti-cancer agents include, but are not limited to: abraxane; ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; b-FGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O_6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific additional active agents include, but are not limited to, oblimersen (GENASENSE®), remicade, docetaxel, celecoxib, melphalan, dexamethasone (DECAD- RON®), steroids, gemcitabine, cisplatinum, temozolomide, etoposide, cyclophosphamide, temodar, carboplatin, procarbazine, gliadel, tamoxifen, topotecan, methotrexate, ARISA®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel, ganciclovir, adriamycin, estramustine sodium phosphate (EM-CYT), sulindac, and etoposide.

5.6 Biological Samples

In certain embodiments, the various methods provided herein use samples (e.g., biological samples) from patients. The patient can be male or female, and can be an adult, child or infant. Samples can be analyzed at a time during an active phase of DLBCL, or when DLBCL is inactive. In one embodiment, a sample is obtained from a patient prior, concurrently with and/or subsequent to administration of a drug described herein. In a specific embodiment, a sample is obtained from a patient prior to administration of a drug described herein. In certain embodiments, more than one sample from a patient can be obtained.

In certain embodiments, the sample used in the methods provided herein comprises body fluids from a subject. Non-limiting examples of body fluids include blood (e.g., peripheral whole blood, peripheral blood), blood plasma, amniotic fluid, aqueous humor, bile, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids, including cerebrospinal fluid surrounding the brain and the spinal cord, synovial fluid surrounding bone joints, intracellular fluid is the fluid inside cells, and vitreous humour the fluids in the eyeball. In some embodiments, the sample is a blood sample. The blood sample can be obtained using conventional techniques as described in, e.g. Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Subpopulations of white blood cells, e.g. mononuclear cells, B cells, T cells, monocytes, granulocytes or lymphocytes, can be further isolated using conventional techniques, e.g. magnetically activated cell sorting (MACS) (Miltenyi Biotec, Auburn, Calif.) or fluorescently activated cell sorting (FACS) (Becton Dickinson, San Jose, Calif.).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0 or 10.0 mL.

In some embodiments, the sample used in the present methods comprises a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. In a specific embodiment, the sample used in the methods described herein comprises a tumor biopsy. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the patient receiving a treatment for DLBCL. In another embodiment, the sample is obtained from the patient during the subject receiving a treatment for the DLBCL. In another embodiment, the sample is obtained from the patient after the patient received a treatment for the DLBCL. In various embodiments, the treatment comprises administering a drug described herein (e.g., see Section 5.4) to the subject.

In certain embodiments, the sample used in the methods provided herein comprises a plurality of cells. Such cells can include any type of cells, e.g., stem cells, blood cells (e.g., peripheral blood mononuclear cells), lymphocytes, B cells, T cells, monocytes, granulocytes, immune cells, or tumor or cancer cells. The tumor or cancer cells or a tumor tissue, such as a tumor biopsy or a tumor explants. T cells (T lymphocytes) include, for example, helper T cells (effector T cells or Th cells), cytotoxic T cells (CTLs), memory T cells, and regulatory T cells. In one embodiment, the cells used in the methods provided herein are CD3$^+$ T cells, e.g., as detected by flow cytometry. The number of T cells used in the methods can range from a single cell to about $10^9$ cells. B cells (B lymphocytes) include, for example, plasma B cells, dendritic cells, memory B cells, B1 cells, B2 cells, marginal-zone B cells, and follicular B cells. B cells can express immunoglobulins (antibodies, B cell receptor).

Specific cell populations can be obtained using a combination of commercially available antibodies (e.g., Quest Diagnostic (San Juan Capistrano, Calif.); Dako (Denmark)).

In certain embodiments, the sample used in the methods provided herein is from a diseased tissue from a DLBCL patient. In certain embodiments, the number of cells used in the methods provided herein can range from a single cell to about $10^9$ cells. In some embodiments, the number of cells used in the methods provided herein is about $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, or $5 \times 10^8$.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

5.7 Methods for Detecting RNA Expression

Several methods of detecting or quantitating mRNA levels are known in the art. Exemplary methods include but are not limited to northern blots, ribonuclease protection assays, PCR-based methods, and the like. The mRNA sequence can be used to prepare a probe that is at least partially complementary. The probe can then be used to detect the mRNA sequence in a sample, using any suitable assay, such as PCR-based methods, Northern blotting, a dipstick assay, and the like.

In other embodiments, a nucleic acid assay for testing for immunomodulatory activity in a biological sample can be prepared. An assay typically contains a solid support and at least one nucleic acid contacting the support, where the nucleic acid corresponds to at least a portion of an mRNA encoded by a gene listed in Table 1, Table 2, or Table 3. The assay can also have a means for detecting the altered expression of the mRNA in the sample.

The assay method can be varied depending on the type of mRNA information desired. Exemplary methods include but are not limited to Northern blots and PCR-based methods (e.g., RT-qPCR). Methods such as RT-qPCR can also accurately quantitate the amount of the mRNA in a sample.

Any suitable assay platform can be used to determine the presence of the mRNA in a sample. For example, an assay may be in the form of a dipstick, a membrane, a chip, a disk, a test strip, a filter, a microsphere, a slide, a multiwell plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4',5' dichloro 2',7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

In some embodiments, the mRNA sequences comprise at least one mRNA selected from the mRNAs encoded by the genes listed in Table 1, Table 2, or Table 3, or a fragment thereof. The nucleic acids may be present in specific, addressable locations on a solid support; each corresponding to at least a portion of mRNA sequences that are differentially expressed upon treatment of an immunomodulatory compound in a cell or a patient.

A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g. under conditions sufficient to provide for specific binding of target mRNAs in the sample to the probes) are described in Kallioniemi et al., *Science* 258:818-821 (1992) and WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to follow the expression of the genes in Table 1, Table 2 or Table 3. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, Real-Time Reverse Transcription-PCR (RT-qPCR) can be used for both the detection and quantification of RNA targets (Bustin, et al., 2005, *Clin. Sci.*, 109:365-379). Quantitative results obtained by RT-qPCR are generally more informative than qualitative data. Thus, in some embodiments, RT-qPCR-based assays can be useful to measure mRNA levels during cell-based assays. The RT-qPCR method is also useful to monitor patient therapy. Examples of RT-qPCR-based methods can be found, for example, in U.S. Pat. No. 7,101,663, which is incorporated by reference herein in its entirety.

In contrast to regular reverse transcriptase-PCR and analysis by agarose gels, real-time PCR gives quantitative results. An additional advantage of real-time PCR is the relative ease and convenience of use. Instruments for real-time PCR, such as the Applied Biosystems 7500, are available commercially, as are the reagents, such as TaqMan Sequence Detection chemistry. For example, TaqMan® Gene Expression Assays can be used, following the manufacturer's instructions. These kits are pre-formulated gene expression assays for rapid, reliable detection and quantification of human, mouse and rat mRNA transcripts. An exemplary PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the CT), the data can be analyzed, for example, using a 7500 Real-Time PCR System Sequence Detection software v1.3 using the comparative CT relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

Techniques known to one skilled in the art may be used to measure the amount of an RNA transcript(s). In some embodiments, the amount of one, two, three, four, five or more RNA transcripts is measured using deep sequencing, such as ILLUMINA® RNASeq, ILLUMINA® next generation sequencing (NGS), ION TORRENT™ RNA next generation sequencing, 454™ pyrosequencing, or Sequencing by Oligo Ligation Detection (SOLID™). In other embodiments, the amount of multiple RNA transcripts is measured using a microarray and/or gene chip. In certain embodiments, the amount of one, two, three or more RNA transcripts is determined by RT-PCR. In other embodiments, the amount of one, two, three or more RNA transcripts is measured by RT-qPCR. Techniques for conducting these assays are known to one skilled in the art. In yet other embodiments, NanoString (e.g., nCounter® miRNA Expression Assays provided by NanoString® Technologies) is used for analyzing RNA transcripts.

5.8 Methods for Detecting Protein Expression

Several protein detection and quantitation methods can be used to measure the level of proteins. Any suitable protein quantitation method can be used. In some embodiments, antibody-based methods are used. Exemplary methods that can be used include but are not limited to immunoblotting (western blot), enzyme-linked immunosorbent assay (ELISA), immunohistochemistry, flow cytometry, cytometric bead array, mass spectroscopy, and the like. Several types of ELISA are commonly used, including direct ELISA, indirect ELISA, and sandwich ELISA.

5.9 Kits

In one aspect, provided herein are pharmaceutical or assay kits comprising a drug described herein (see, Section 5.4) or a pharmaceutical composition thereof, in one or more containers, and instructions for use. In certain embodiments, the kits useful for predicting the responsiveness of a DLBCL patient to a drug described herein. In further embodiments, the drug, in a container, is accompanied by an apparatus or apparati necessary for administering the drug or composition thereof to a subject. In some embodiments, the instructions provided herein provide a score or threshold level of expression or an output of a functional transformation applied to expression that a gene or subset of genes needs to be achieved in order to indicate that the DLBCL patient will be responsive to the drug described herein.

In certain embodiments, a kit comprises a drug described herein or pharmaceutical composition thereof, in a container, and a reagent or reagents necessary for carrying out an assay(s) described herein, in one or more other containers. In certain embodiments, the kit comprises a solid support, and a means for detecting the RNA or protein expression of at least one biomarker (e.g., a differentially expressed gene identified in Table 1, 2 or 3) in a biological sample. Such a kit may employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide.

In a specific embodiment, the pharmaceutical or assay kit comprises, in a container, a drug described herein or a pharmaceutical composition thereof, and further comprises, in one or more containers, components for isolating RNA. In another specific embodiment, the pharmaceutical or assay kit comprises, in a container, a drug described herein or a pharmaceutical composition, and further comprises, in one or more containers, components for conducting RT-PCR, RT-qPCR, deep sequencing, or a microarray such as NanoString assay. In some embodiments, the kit comprises a solid support, nucleic acids contacting the support, where the nucleic acids are complementary to at least 20, 50, 100, 200, 350, or more bases of mRNA, and a means for detecting the expression of the mRNA in a biological sample.

In another specific embodiment, the pharmaceutical or assay kit comprises, in a container, a drug described herein or a pharmaceutical composition thereof, and further comprises, in one or more containers, components for isolating protein. In another specific embodiment, the pharmaceutical or assay kit comprises, in a container, a drug described herein or a pharmaceutical composition, and further comprises, in one or more containers, components for conducting flow cytometry or an ELISA.

In another aspect, provided herein are kits for measuring biomarkers providing the materials necessary to measure the abundance of one or more of the gene products of the genes or a subset of genes (e.g., one, two, three, four, five or more genes) in Table 1, 2 or 3, or any combination thereof. Such kits may comprise materials and reagents required for measuring RNA or protein. In some embodiments, such kits include microarrays, wherein the microarray is comprised of oligonucleotides and/or DNA and/or RNA fragments which hybridize to one or more of the products of one or more of the genes or a subset of genes in Table 1, 2 or 3, or any combination thereof. In some embodiments, such kits may include primers for PCR of either the RNA product or the cDNA copy of the RNA product of the genes or subset of genes, or both. In some embodiments, such kits may include primers for PCR as well as probes for Quantitative PCR. In some embodiments, such kits may include multiple primers and multiple probes wherein some of said probes have different flourophores so as to permit multiplexing of multiple products of a gene product or multiple gene products. In some embodiments, such kits may further include materials and reagents for creating cDNA from RNA. In some embodiments, such kits may include antibodies specific for the protein products of a gene or subset of genes in Table 1, 2 or 3, or any combination thereof. Such kits may additionally comprise materials and reagents for isolating RNA and/or proteins from a biological sample. In addition such kits may include materials and reagents for synthesizing cDNA from RNA isolated from a biological sample. In some embodiments, such kits may include, a computer program product embedded on computer readable media for predicting whether a patient is responsive to a drug as described herein. In some embodiments, the kits may include a computer program product embedded on a computer readable media along with instructions.

In some embodiments, kits for measuring the expression of one or more nucleic acid sequences of a gene or a subset of genes in Table 1, 2 or 3 or a combination thereof. In a specific embodiment, such kits measure the expression of one or more nucleic acid sequences associated with a gene or a subset of genes in Table 1, 2 or 3 or a combination thereof. In accordance with this embodiment, the kits may comprise materials and reagents that are necessary for measuring the expression of particular nucleic acid sequence products of genes or a subset of genes in Table 1, 2 or 3, or a combination thereof. For example, a microarray or RT-PCR kit may be produced for a specific condition and contain only those reagents and materials necessary for measuring the levels of specific RNA transcript products of the genes or a subset of genes in Table 1, 2 or 3, or a combination thereof to predict whether a DLBCL patient is response to treatment with a drug described herein. Alternatively, in some embodiments, the kits can comprise materials and reagents that are not limited to those required to measure the expression of particular nucleic acid sequences of any particular gene in Table 1, 2 or 3, or a combination thereof. For example, in certain embodiments, the kits comprise materials and reagents necessary for measuring the levels of expression of 1, 2, 3, 4, 5, 6, 7, 8, 9, 10, 11, 12, 13, 14, 15, 16, 17, 18, 19, 20, 21, 22, 23, 24, 25 or 26 of the genes in Table 1, 2 or 3, in addition to reagents and materials necessary for measuring the levels of the expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 60, at least 70, or more genes other than those in Table 1, 2 or 3. In other embodiments, the kits contain reagents and materials necessary for measuring the levels of expression of at least 1, at least 2, at least 3, at least 4, at least 5, at least 6, at least 7, at least 8, at least 9, at least 10, at least 11, at least 12, at least 13, at least 14, at least 15, at least 15, at least 17, at least 18, at least 19, at least 20, at least 21, at least 22, at least 23, at least 24, at least 25, or more of the genes in Table 1, 2 or 3, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are genes not in Table 1, 2 or 3, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are genes not in Table 1, 2 or 3.

For nucleic acid microarray kits, the kits generally comprise probes attached to a solid support surface. In one such embodiment, probes can be either oligonucleotides or longer length probes including probes ranging from 150 nucleotides in length to 800 nucleotides in length. The probes may be labeled with a detectable label. In a specific embodiment, the probes are specific for one or more of the gene products in Table 1, 2 or 3. The microarray kits may comprise instructions for performing the assay and methods for interpreting and analyzing the data resulting from the performance of the assay. In a specific embodiment, the kits comprise instructions for predicting whether a DLBCL patient is responsive to treatment with a drug described herein. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

In certain embodiments, a nucleic acid microarray kit comprises materials and reagents necessary for measuring the levels of expression of 1, 2, 3, 4, 5, 6, 7, 8, 9, 10, 11, 12, 13, 14, 15, 16, 17, 18, 19, 20, 21, 22, 23, 24, 25, 26 or more of the genes identified in Table 1, 2 or 3, or a combination thereof, in addition to reagents and materials necessary for measuring the levels of the expression of at least 1, at least 2, at least 3, at least 4, at least 5, at least 6, at least 7, at least 8, at least 9, at least 10, at least 11, at least 12, at least 13, at least 14, at least 15, at least 15, at least 17, at least 18, at least 19, at least 20, at least 21, at least 22, at least 23, at least 24, at least 25, or more genes other than those in Table 1, 2 or 3. In other embodiments, a nucleic acid microarray kit contains reagents and materials necessary for measuring the levels of expression of at least 1, at least 2, at least 3, at least 4, at least 5, at least 6, at least 7, at least 8, at least 9, at least 10, at least 11, at least 12, at least 13, at least 14, at least 15, at least 15, at least 17, at least 18, at least 19, at least 20, at least 21, at least 22, at least 23, at least 24, at least 25, or more of the genes in Table 1, 2 or 3, or any combination thereof, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not in Table 1 or 17, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not in Table 1, 2 or 3.

For Quantitative PCR, the kits generally comprise preselected primers specific for particular nucleic acid sequences. The Quantitative PCR kits may also comprise enzymes suitable for amplifying nucleic acids (e.g., polymerases such as Taq), and deoxynucleotides and buffers needed for the reaction mixture for amplification. The Quantitative PCR kits may also comprise probes specific for the nucleic acid sequences associated with or indicative of a condition. The probes may or may not be labeled with a flourophore. The probes may or may not be labeled with a quencher molecule. In some embodiments the Quantitative PCR kits also comprise components suitable for reverse-transcribing RNA including enzymes (e.g., reverse transcriptases such as AMV, MMLV and the like) and primers for reverse transcription along with deoxynucleotides and buffers needed for the reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the assay and methods for interpreting and analyzing the data resulting from the performance of the assay. In a specific embodiment, the kits contain instructions for predicting whether a DLBCL patient is responsive to a drug described herein.

For antibody based kits, the kit can comprise, for example: (1) a first antibody (which may or may not be attached to a solid support) which binds to a peptide, polypeptide or protein of interest; and, optionally, (2) a second, different antibody which binds to either the peptide, polypeptide or protein, or the first antibody and is conjugated to a detectable label (e.g., a fluorescent label, radioactive isotope or enzyme). In a specific embodiment, the peptide, polypeptide or protein of interest is associated with or indicative of a condition (e.g., a disease). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. In a specific embodiment, the kits contain instructions for predicting whether a DLBCL patient is responsive to treatment with a drug described herein.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method for treating a human diffuse large B-cell lymphoma (DLBCL) patient comprising:
    (a) obtaining a first biological sample from a lymph-node biopsy of a human DLBCL patient;
    (b) determining the nucleic acid expression levels of
        (i) all genes from the group consisting of C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, and ZNF215;
        (ii) all genes from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, and ZNF506; or
        (iii) all genes from the group consisting of BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1;
    (c) classifying the patient as a responsive patient to the treatment of a drug using the nucleic acid expression levels determined in step (b) as compared to nucleic acid expression levels of the same genes in DLBCL patients whose responsiveness to the drug is known;
    wherein the drug is 3-(4-amino-1-oxo-1,3-dihydro-isoindol-2-yl)-piperidine-2,6-dione (lenalidomide); 3-(5-amino-2-methyl-4-oxo-4H-quinazolin-3-yl)-piperidine-2,6-dione (Compound A); or a stereoisomer thereof; or a pharmaceutically acceptable salt, solvate, hydrate, co-crystal, clathrate thereof; or a polymorph thereof;
    (d) administering the drug to the responsive patient to the treatment of the drug as classified in step (c).

2. The method of claim 1, wherein the determining step comprises detecting the presence and/or amount of a hybridization complex in the biological sample, wherein the presence and/or amount of the complex indicates the nucleic acid expression levels of: all genes from the group consisting of C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, and ZNF215; genes from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, and ZNF506; or all genes from the group consisting of BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1.

3. The method of claim 1, wherein the determining step comprises detecting the presence and/or amount of a reaction product in the biological sample, wherein the presence and/or amount of the reaction product indicates the nucleic acid expression levels of: all genes from the group consisting of C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, and ZNF215; all genes from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, and ZNF506; or all genes from the group consisting of BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1.

4. The method of claim 1, wherein the DLBCL is refractory or relapsed.

5. The method of claim 1, wherein the DLBCL is a germinal center B-cell-like subtype.

6. The method of claim 1, wherein the DLBCL is activated B-cell like.

7. The method of claim 1, wherein the DLBCL is Type III.

8. The method of claim 1, wherein the method comprises:
    (b) determining the expression level of all genes from the group consisting of C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, and ZNF215; and
    (c) classifying the patient as a responsive patient based on the expression levels of all genes from the group consisting of C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, and ZNF215.

9. The method of claim 1, wherein the method comprises:
(b) determining the expression level of all genes from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, and ZNF506; and
(c) classifying the patient as a responsive patient based on the expression levels of all genes from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, and ZNF506.

10. The method of claim 1, wherein the method comprises
(b) determining the expression level of all genes from the group consisting of BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1; and
(c) classifying the patient as a responsive patient based on the expression levels of all genes from the group consisting of BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1.

11. The method of claim 1, wherein the classifying step comprises a computational decision function based on nucleic acid expression levels of all genes from the group consisting of C10orf54, C1RL, C20orf112, C8orf4, CCDC88C, CILP, CIRH1A, CLU, CPVL, CSF1R, CTSB, EPB41L3, FBXO32, IFI44, LRP11, MEGF6, MEIS1, PHACTR2, PLAT, SERPING1, SPC25, THEMIS2, TPSAB1, ULK1, XAF1, and ZNF215; all genes from the group consisting of ANXA4, BACH2, BIN2, C7orf10, CXCL14, DAPL1, FBXO32, FCGR1B, FTX, GIMAP6, IL18BP, KCNMB1, KIAA1671, LOC284837, MPP6, MZT1, NFIC, ODF3B, OLFM1, PPAT, RFESD, RPL22L1, SERPING1, TNC, TNFRSF17, and ZNF506; or all genes from the group consisting of BMS1P20, MZB1, TNFRSF17, FKBP11, IGLV1-44, MS4A1, BCL11A, MACROD2, FAM129C, ALDH2, KIAA1598, TGFBI, TYMP, SAMD4A, GPX3, A2M, CFB, FSTL1, SLC27A3, and NRP1 in DLBCL patients whose responsiveness to the drug is known.

* * * * *